United States Patent
Kashfi et al.

(10) Patent No.: US 10,071,981 B2
(45) Date of Patent: Sep. 11, 2018

(54) METHOD OF PRIMING PLANTS AGAINST ABIOTIC STRESS FACTORS

(71) Applicants: Research Foundation of The City University of New York, New York, NY (US); Cyprus University of Technology, Lemesos (CY)

(72) Inventors: Khosrow Kashfi, Dix Hills, NY (US); Vasileios Fotopoulos, Limassol (CY)

(73) Assignees: RESEARCH FOUNDATION OF THE CITY UNIVERSITY OF NEW YORK, New York, NY (US); CYPRUS UNIVERSITY OF TECHNOLOGY, Limassol (CY)

( * ) Notice: Subject to any disclaimer, the term of this patent is extended or adjusted under 35 U.S.C. 154(b) by 0 days.

(21) Appl. No.: 15/115,959

(22) PCT Filed: Feb. 11, 2015

(86) PCT No.: PCT/US2015/015380
§ 371 (c)(1),
(2) Date: Aug. 2, 2016

(87) PCT Pub. No.: WO2015/123273
PCT Pub. Date: Aug. 20, 2015

(65) Prior Publication Data
US 2017/0174651 A1    Jun. 22, 2017

Related U.S. Application Data

(60) Provisional application No. 62/006,295, filed on Jun. 2, 2014, provisional application No. 61/939,064, filed on Feb. 12, 2014.

(51) Int. Cl.
*C07D 339/04* (2006.01)
*A01N 43/26* (2006.01)

(52) U.S. Cl.
CPC ........... *C07D 339/04* (2013.01); *A01N 43/26* (2013.01)

(58) Field of Classification Search
CPC ...... A01N 43/26; C07D 339/04; A61K 31/24; A61K 31/385
USPC ...................................................... 504/290
See application file for complete search history.

(56) References Cited

FOREIGN PATENT DOCUMENTS

WO    WO2013025790 A2    2/2013

OTHER PUBLICATIONS

Shaowei Li et al. ,Letters in Drug Design and Discovery, 2014,11,98-103.*
Li et al., "Synthesis and Bio-Evaluation of Novel Salicylic Acid-Oriented Thiourea Derivatives with Potential Applications in Agriculture", Letters in Drug Design & Discovery, 11, 98-103 (2014).
Rivas-San Vicente et al., "Salicylic Acid Beyond Defence: Its Role in Plant Growth and Development", Journal of Experimental Botany, vol. 62, No. 10. pp. 3321-3338 (2011).
Chattopadhyay et al., "NOSH-Aspirin (NBS-1120), a Novel Nitric Oxide- and Hydrogen Sulfide-Releasing Hybrid is a Potent Inhibitor of Colon Cancer Cell Growth in Vitro and in a Xenograft Mouse Model", Biochemical and Biophysical Research Communications 419, 523-528 (2012).
Antoniou et al., "Exploring the Potential of NOSH-Aspirin as a Plant Priming Agent Against Abiotic Stress Factors", Abstracts/ Nitric Oxide 39, S16-S49 (2014).
Supplemental European Search Report for corresponding European Application EP 15749116, pp. 1-14 (Sep. 4, 2017).
Nazar et al., "Salicylic Acid Alleviates Decreases in Photosynthesis Under Salt Stress by Enhancing Nitrogen and Sulfur Assimilation and Antioxidant Metabolism Differentially in Two Mungbean Cultivars", Journal of Plant Physiology, pp. 807-815 (2011).
Shi et al., "Nitric Oxide-Activated Hydrogen Sulfide is Essential for Cadmium Stress Response in Bermudagrass (*Cynodon dactylon* (L). Pers.)", Plant Physiology and Biochemistry, vol. 74, pp. 99-107 (2014).
International Search Report for corresponding International Application No. PCT/US15/15380, pp. 1-3 (dated Jun. 26, 2015).

* cited by examiner

*Primary Examiner* — Johann R Richter
*Assistant Examiner* — Courtney A Brown
(74) *Attorney, Agent, or Firm* — Hoffmann & Baron, LLP

(57) ABSTRACT

A method of reducing cellular damage to a plant by treating the plant with a compound containing an NO-releasing moiety and an $H_2S$-releasing moiety covalently bonded to an aspirin derived core or a NOSH compound is claimed. The compounds may also be used in a method of priming a plant against abiotic stress factors and a method of promoting plant growth.

19 Claims, 19 Drawing Sheets

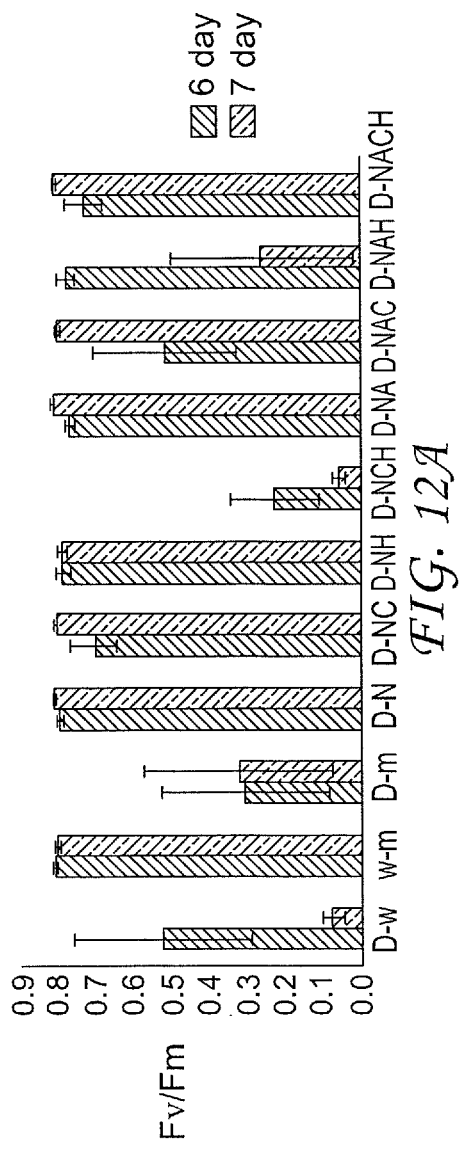
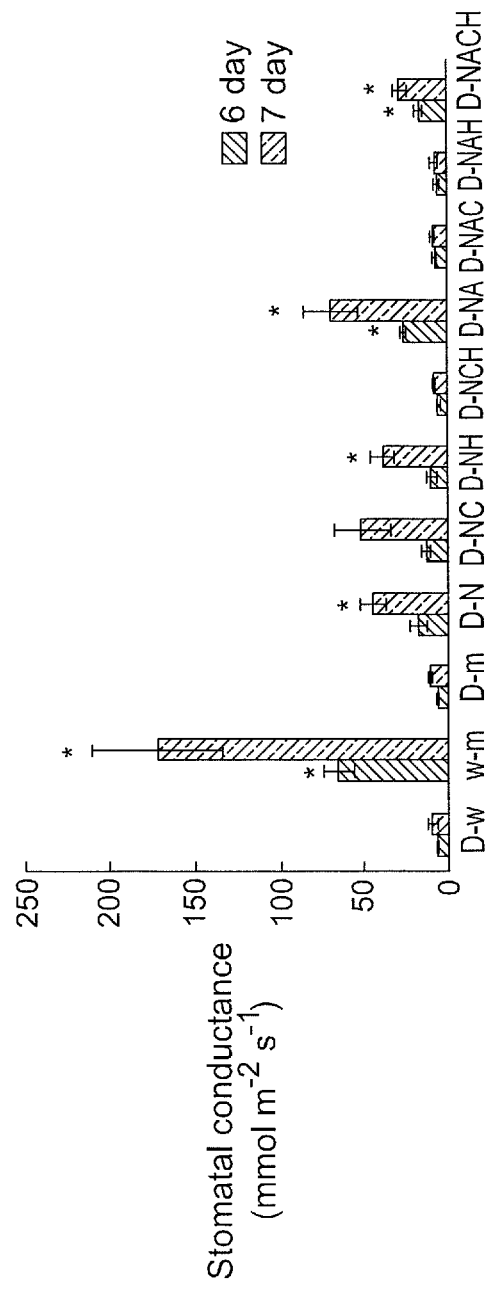
FIG. 12A
FIG. 12B

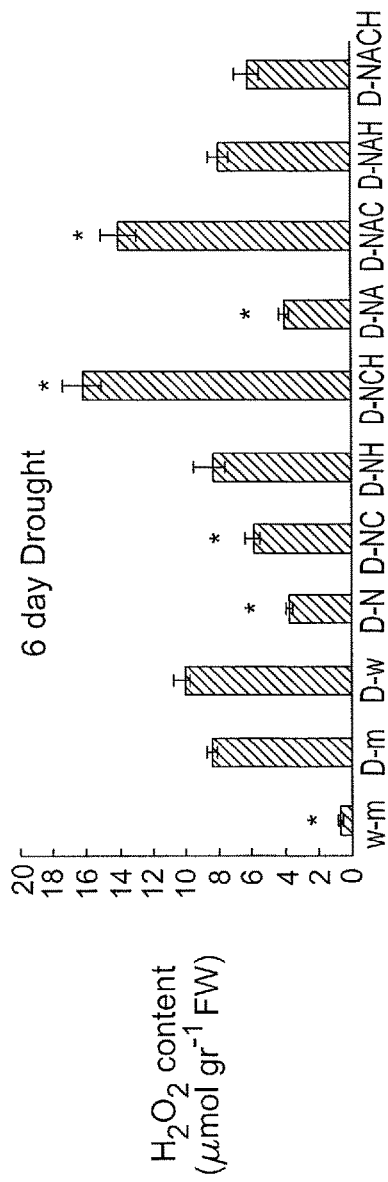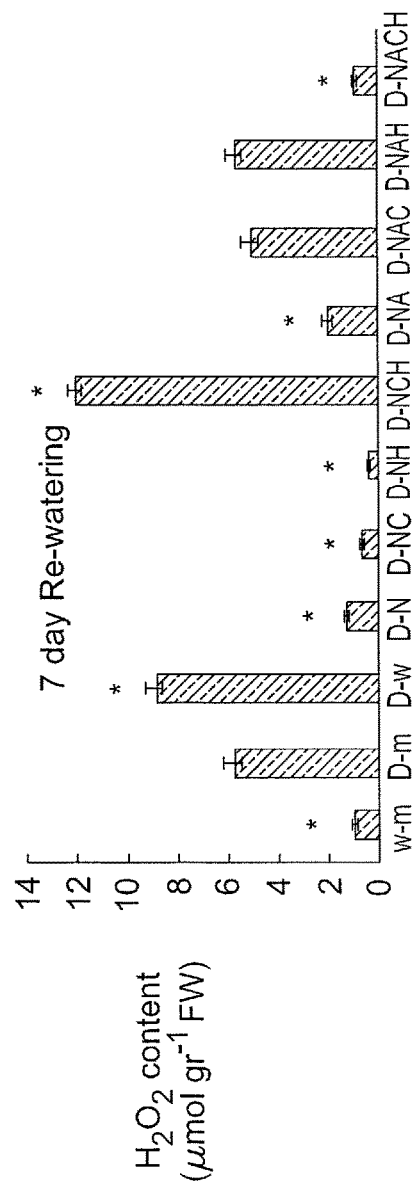
FIG. 14A-1
FIG. 14A-2

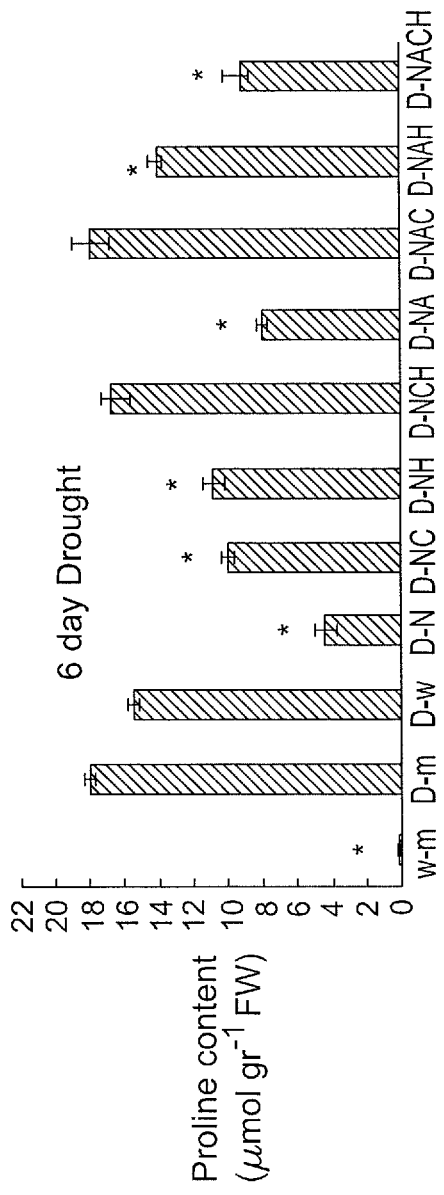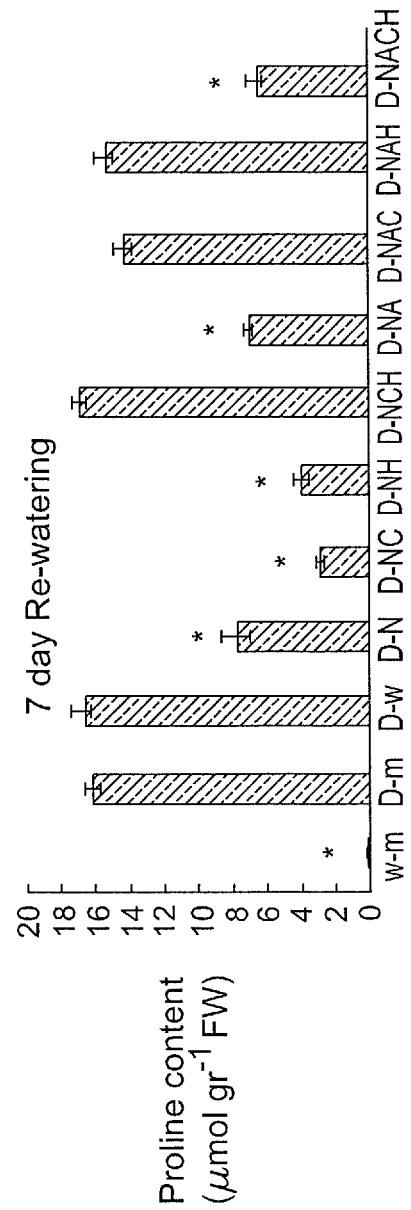
FIG. 15A
FIG. 15B

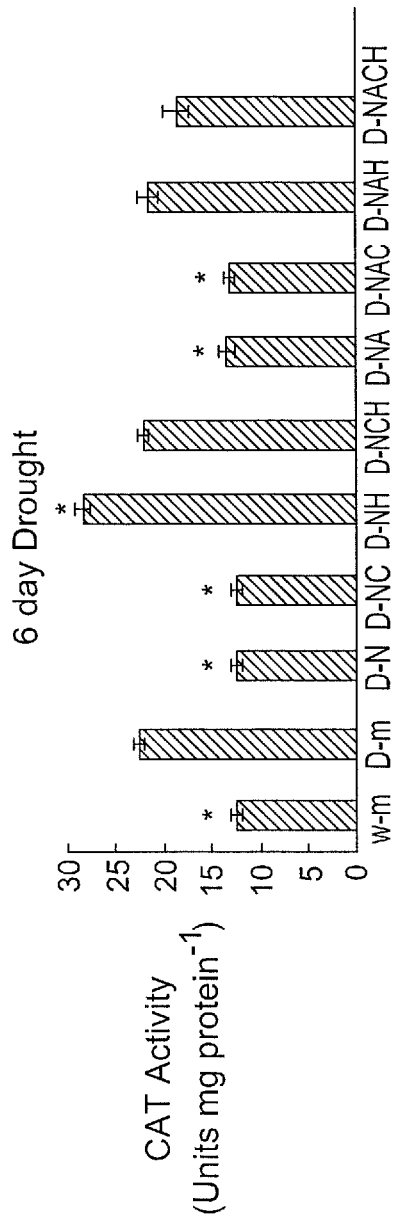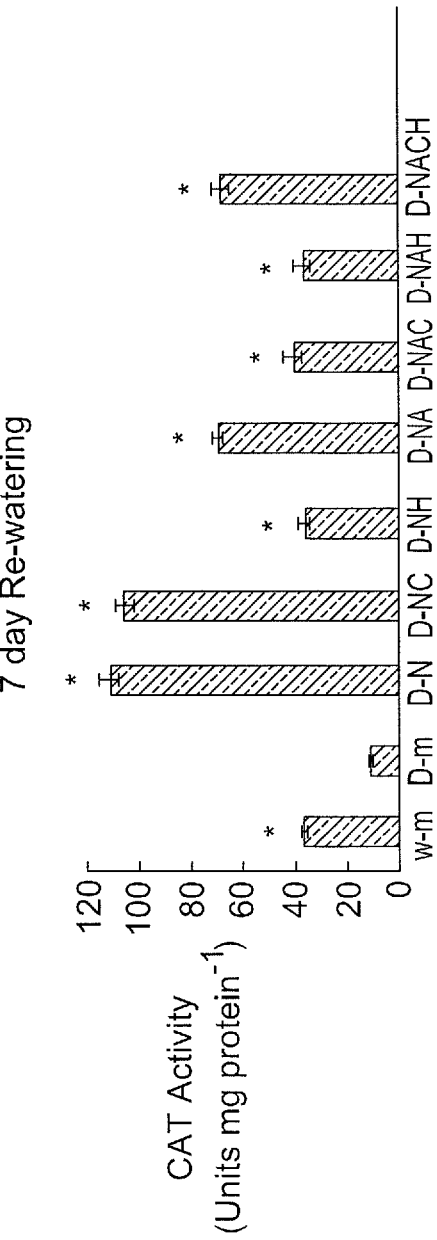

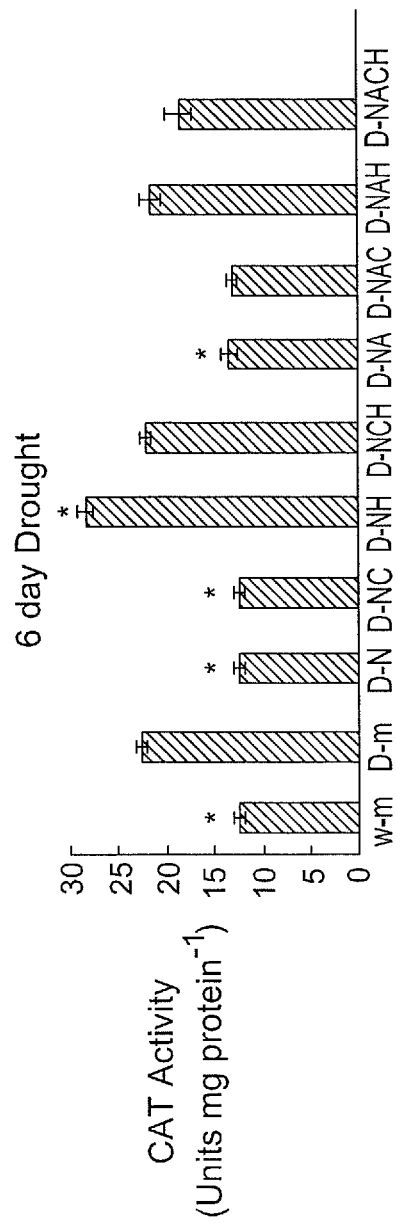
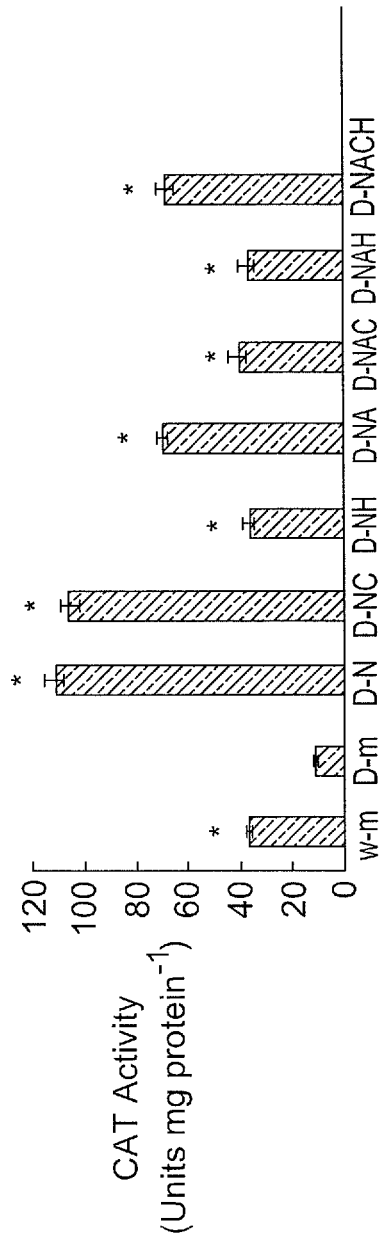
FIG. 16B-1
FIG. 16B-2

METHOD OF PRIMING PLANTS AGAINST ABIOTIC STRESS FACTORS

CROSS-REFERENCE TO RELATED APPLICATIONS

This application claims the benefit of PCT Application No. PCT/US2015/015380, filed Feb. 11, 2015, which claims the benefit of U.S. Provisional Patent Application Ser. Nos. 61/939,064, filed Feb. 12, 2014, and 62/006,295, filed Jun. 2, 2014. The entire contents of which are incorporated herein by reference.

BACKGROUND OF THE INVENTION

Abiotic stress factors such as drought, salinity, and heat represent key elements limiting agricultural productivity worldwide. Close examination of plant-to-plant communication in nature has revealed the development of unique strategies from plants for responding to abiotic stress, with one of the most interesting being through priming for improved defense responses. The process of priming involves prior exposure to a biotic or abiotic stress factor making a plant more resistant to future exposure. Priming can also be achieved by applying natural or synthetic compounds which act as signaling transducers, 'activating' the plant's defense system. Although the phenomenon has been known for many years, it has only recently been suggested that priming can enhance the resistance of crops to environmental stresses in the field.

There is a need for new priming agents that work better to prepare plants for exposure to abiotic stress factors.

There is also a need for new cost-effective means of promoting plant growth from the time of seeding throughout the maturity of a plant.

SUMMARY OF THE INVENTION

The invention relates to a method of reducing cellular damage to a plant including treating the plant with a composition including a compound containing an NO-releasing moiety and an H$_2$S-releasing moiety covalently bonded to an aspirin derived core. In a preferred embodiment, the compound containing an NO-releasing moiety and an H$_2$S-releasing moiety covalently bonded to an aspirin derived core is of formula I:

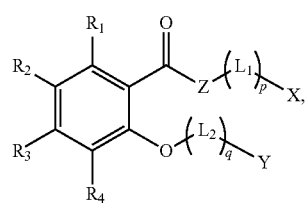

wherein:
each of p and q, independently, is 0 or 1;
each of L$_1$ and L$_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7;

X is a H$_2$S-releasing moiety or a NO-releasing moiety;
Y is a NO-releasing moiety or a H$_2$S-releasing moiety, provided that X and Y are not simultaneously H$_2$S-releasing moieties or NO-releasing moieties;
Z is O or NH; and
each of R$_1$, R$_2$, R$_3$, and R$_4$, independently, is H, halo, C$_1$-C$_{10}$ alkyl, or N(R)$_2$, in which R is H or C$_1$-C$_{10}$ alkyl.

Preferably, the H$_2$S-releasing moiety is

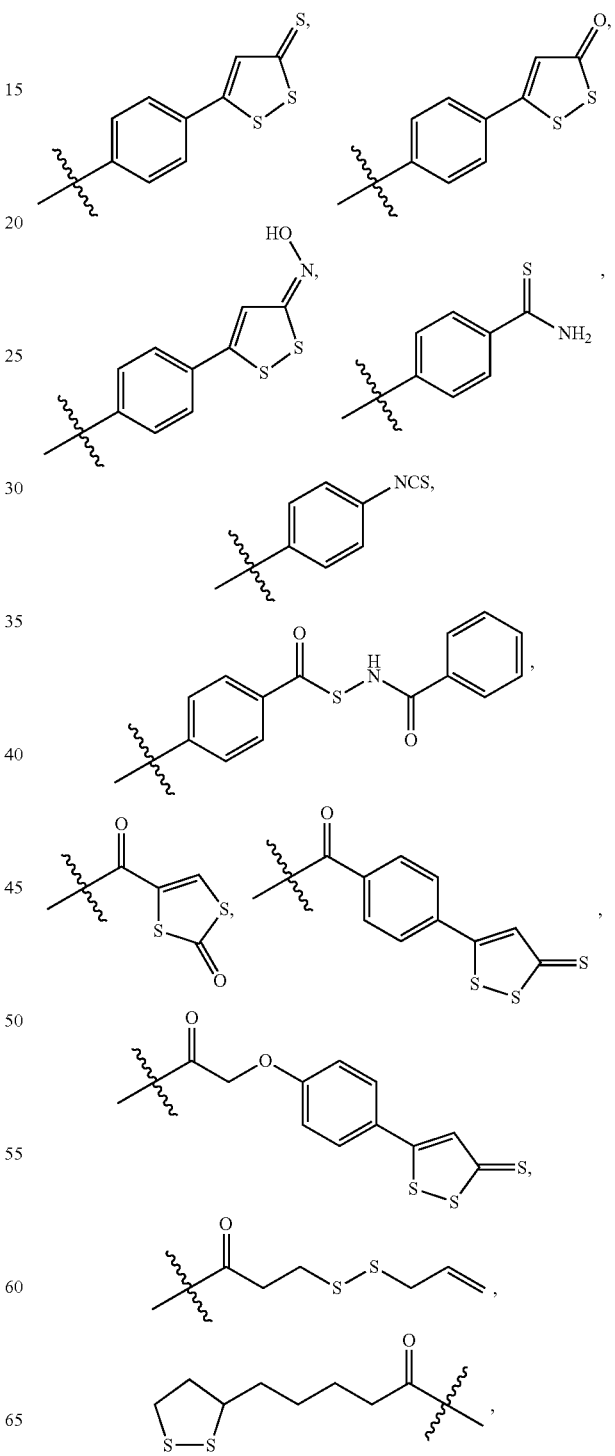

3
-continued
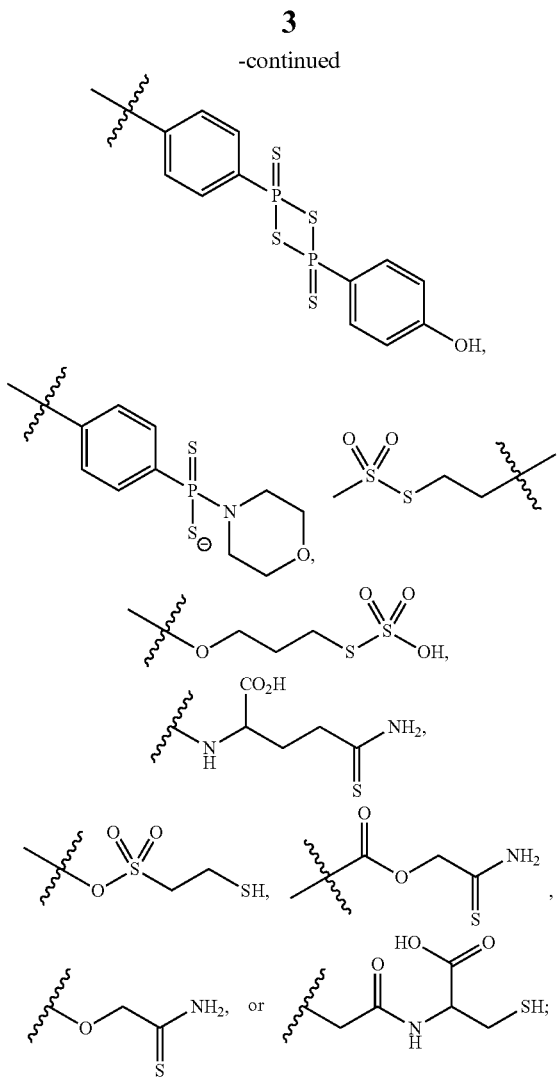
and
the NO-releasing moiety is —NO, —C(O)—(CH$_2$)$_n$—ONO$_2$, —O—(CH$_2$)$_n$—ONO$_2$, —(CH$_2$)$_n$—ONO$_2$, —C(O)—CH$_2$—C(CH$_3$)$_2$—SNO, —NH—CH$_2$—C(CH$_3$)$_2$—SNO, —CH$_2$—C(CH$_3$)$_2$—SNO,
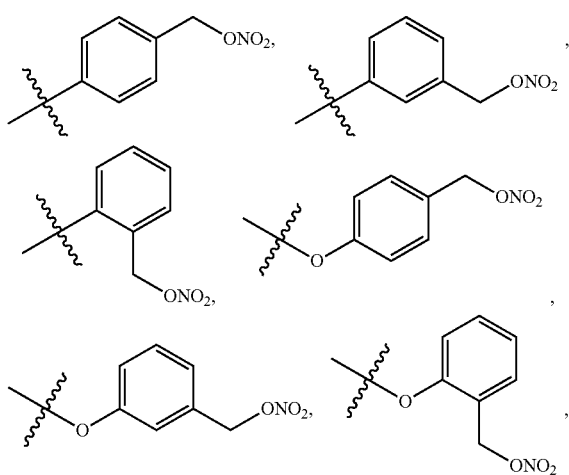
4
-continued
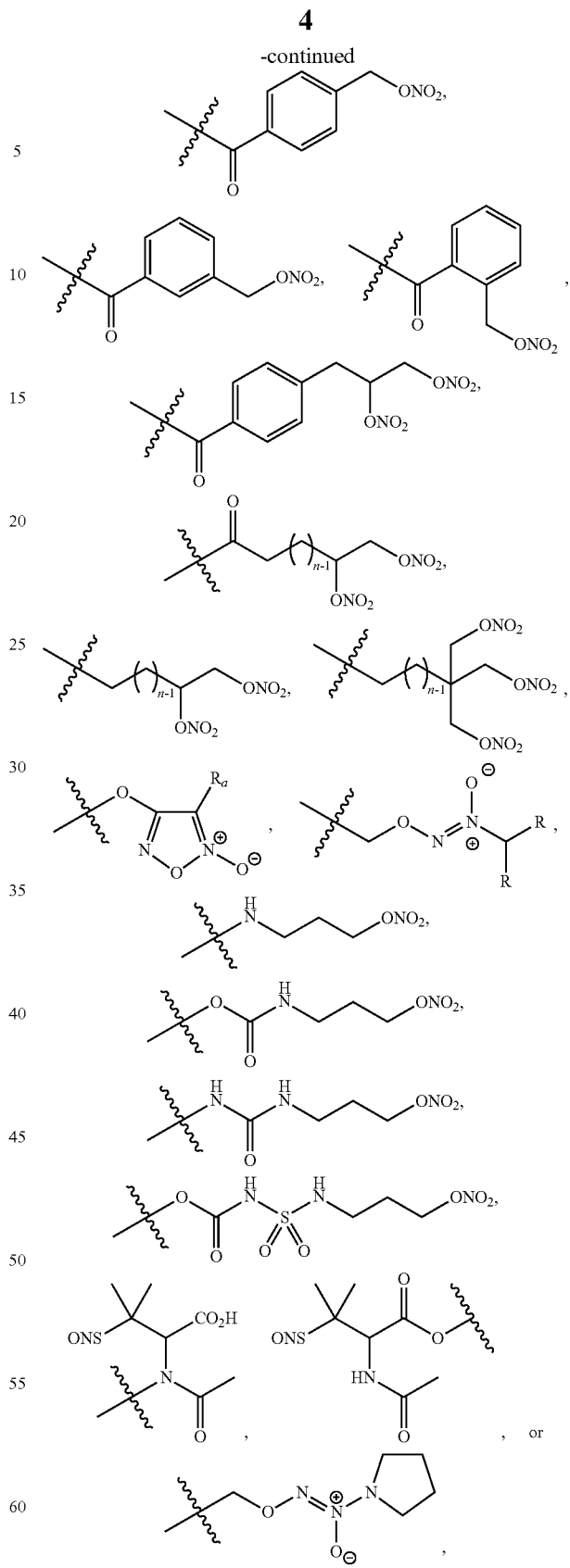
in which n is 1, 2, 3, 4, 5, 6, or 7; R$_a$ is H, C$_1$-C$_{10}$ alkyl, aryl, S(O)$_2$-aryl, CN, or CON(R$_b$)$_2$; and each R$_b$, independently, is H or C$_1$-C$_{10}$ alkyl.

In another preferred embodiment, X is

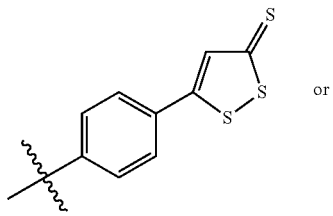

or

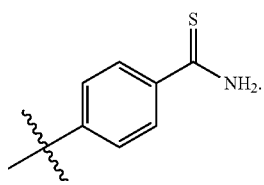

Y is preferably —C(O)—(CH$_2$)$_n$—ONO$_2$.

Preferred compounds of the invention include:

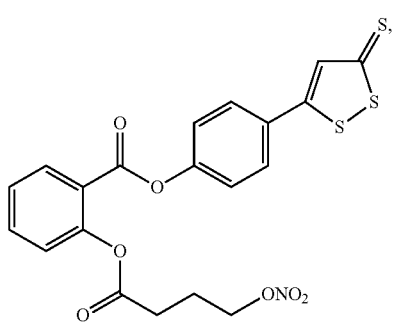

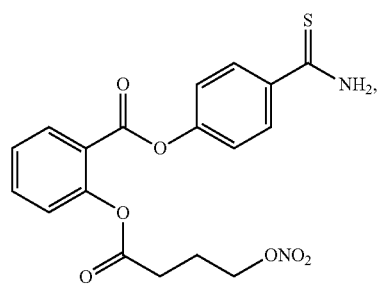

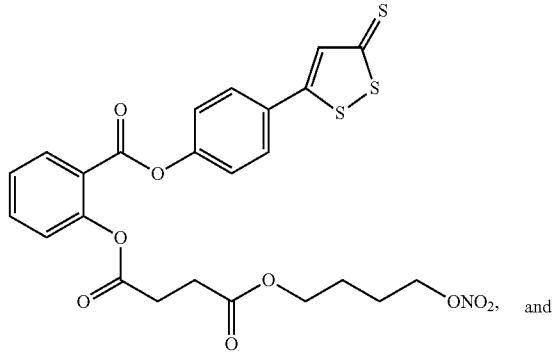

and

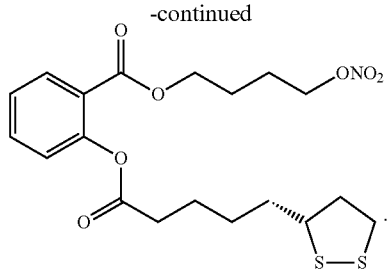

The invention also relates to a method of priming a plant against abiotic stress factors including treating the plant with a composition including a compound containing an NO-releasing moiety and an H$_2$S-releasing moiety covalently bonded to an aspirin derived core. The abiotic stress factor is preferably drought, salinity, heat, or combinations thereof. Preferred compounds are described above.

The compound below, NOSH, may also be used in a composition to reduce cellular damage to a plant

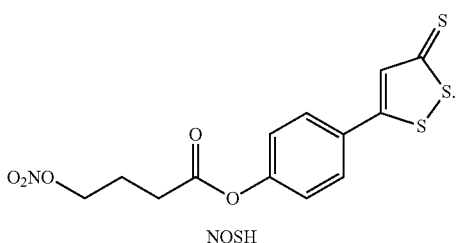

NOSH

NOSH may also be used in a composition to prime a plant against abiotic stress factors.

The invention also relates to a method of promoting growth of a plant including treating the plant with a composition including a compound containing an NO-releasing moiety and an H$_2$S-releasing moiety covalently bonded to an aspirin derived core or NOSH. Preferred compounds are described above.

DESCRIPTION OF THE DRAWINGS

FIG. 12 Chlorophyll fluorescence and stomatal conductance levels of plants at 6 d (drought stress) and 7 d (recovery).

FIG. 14 Hydrogen peroxide (A) and nitric oxide (B) content in leaves of drought-stressed *M. sativa* plants in the presence or absence of NOSH/NOSH-aspirin pretreatment at 6 d (drought stress) and 7 d (recovery).

FIG. 15 Proline content in leaves of drought-stressed *M. sativa* plants in the presence or absence of NOSH/NOSH-aspirin pretreatment at 6 d (drought stress) and 7 d (recovery).

FIG. 16 Superoxide dismutase (SOD; A) and catalase (CAT; B) enzymatic activity in leaves of drought-stressed *M. sativa* plants in the presence or absence of NOSH/NOSH-aspirin pretreatment at 6 d (drought stress) and 7 d (recovery).

DETAILED DESCRIPTION

Figure 1:
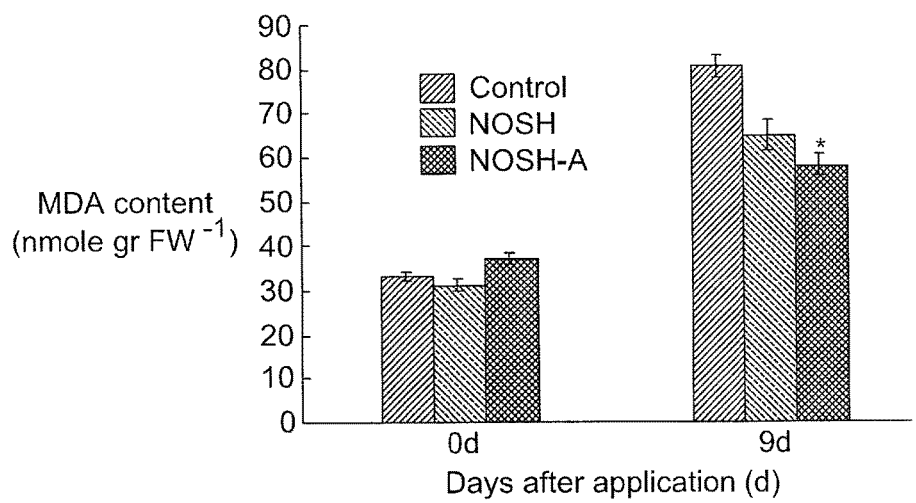
FIG. 1 Cellular damage indicated by leaf MDA content in drought-stressed *M. truncatula* plants in the presence or absence of NOSH/NOSH-aspirin pre-treatment (dissolved in 70% (v/v) MetOH) (n=3).

In one embodiment, the invention relates to reducing cellar damage to a plant comprising treating the plant with a composition comprising a compound containing an NO-releasing moiety and an $H_2S$-releasing moiety covalently bonded to an aspirin derived core. The plant may be any type of plant. Preferred plants are terrestrial plants since they are most adversely affected by abiotic stress factors such as drought, salinity, and heat.

Compounds containing an NO-releasing moiety and an $H_2S$-releasing moiety covalently bonded to an aspirin derived core are known in the art. See International Patent Publication No. WO 2013/025790, the contents of which are incorporated by reference herein.

In a preferred embodiment, the compound is of formula (I):

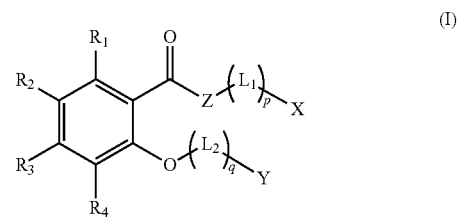

wherein each of p and q, independently, is 0 or 1; each of $L_1$ and $L_2$, independently, is a linker, the linker being —C(O)—, —$(CH_2)_m$—, —$(CH_2)_m$—O—, —$(CH_2)_m$—C(O)—, —$(CH_2)_m$—C(O)O—, —$(CH_2)_m$—OC(O)O—, —C(O)—$(CH_2)_m$—O—, —C(O)—$(CH_2)_m$—C(O)—, —OC(O)—$(CH_2)_m$—O—, —OC(O)—$(CH_2)_m$—C(O)—, or —OC(O)—$(CH_2)_m$—C(O)O—, in which m is 1, 2, 3, 4, 5, 6, or 7; X is a $H_2S$-releasing moiety or a NO-releasing moiety; Y is a NO-releasing moiety or a $H_2S$-releasing moiety, provided that X and Y are not simultaneously $H_2S$-releasing moieties or NO-releasing moieties; Z is O or NH; and each of $R_1$, $R_2$, $R_3$, and $R_4$, independently, is H, halo, $C_1$-$C_{10}$ alkyl, or $N(R)_2$, in which R is H or $C_1$-$C_{10}$ alkyl.

In a subset of the compounds of formula (I), X can be

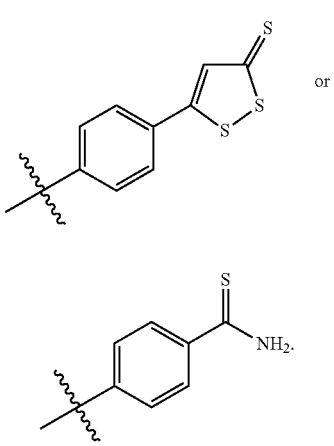

In some embodiments of such compounds, Y can be —C(O)—$(CH_2)_n$—$ONO_2$, and p and q can be 0. Examples of such compounds are (NOSH-1)

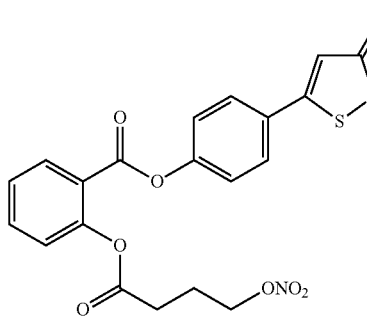

and p and q can be 0. An example of such compounds is (NOSH-4)

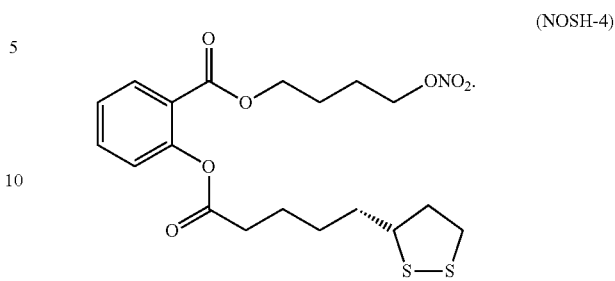

Other examples of the compounds of formula (I) include:

(NOSH-3)

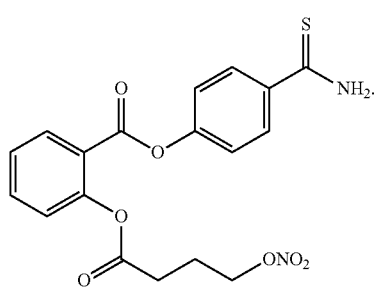

NOSH-1 is also referred to herein as NOSH-aspirin, NOSH-A, or NOSHA. In some embodiments of such compounds, Y can be —$(CH_2)_n$—$ONO_2$, p can be 0, q can be 1, and $L_2$ can be —OC(O)—$(CH_2)_m$—C(O)—. An example of such a compound is

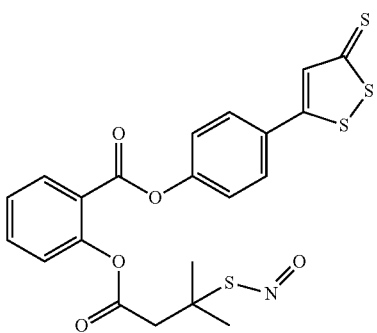

(NOSH-2)

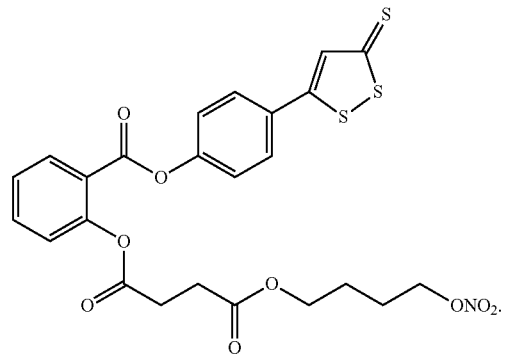

In another subset of the compounds of formula (I), X can be —C(O)—$(CH_2)_n$—$ONO_2$. In such a compound, Y can be

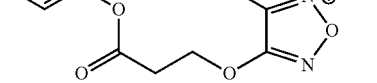

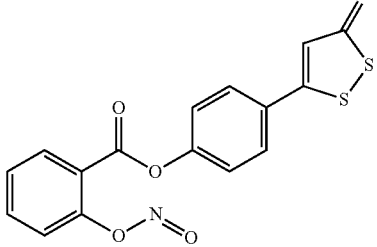

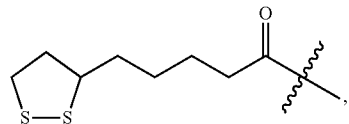 [SMILES: *C(=O)CCCCC1CCSS1]

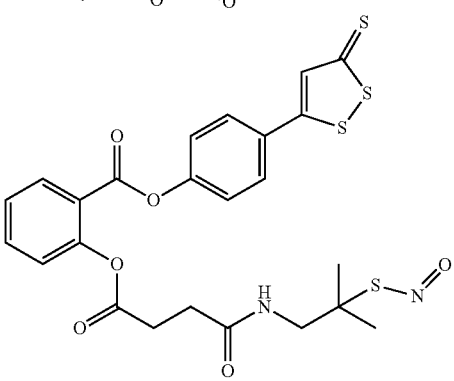

11
-continued
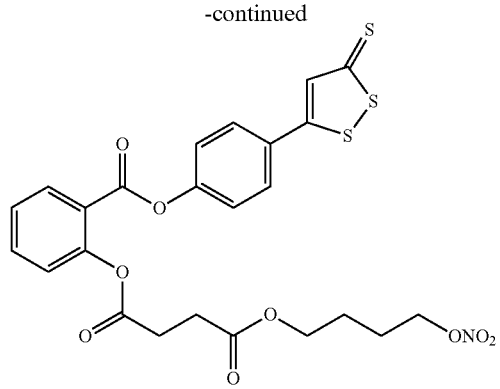
12
-continued
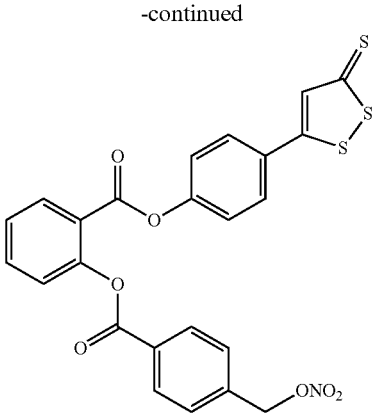
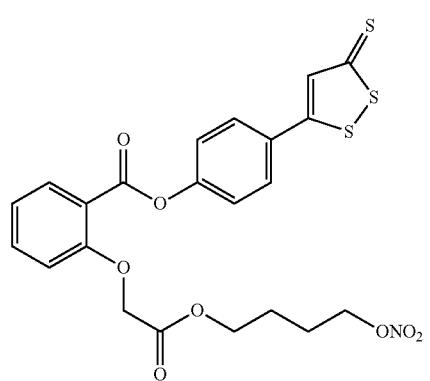
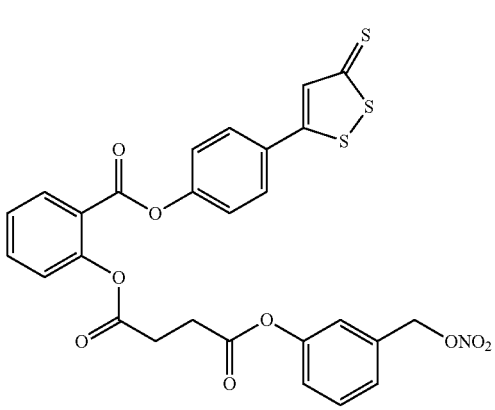
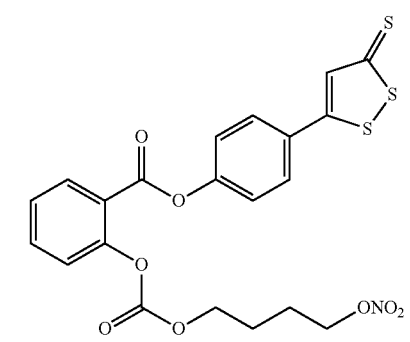
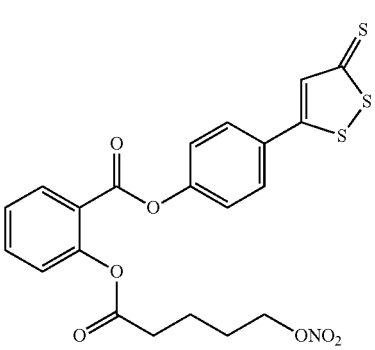
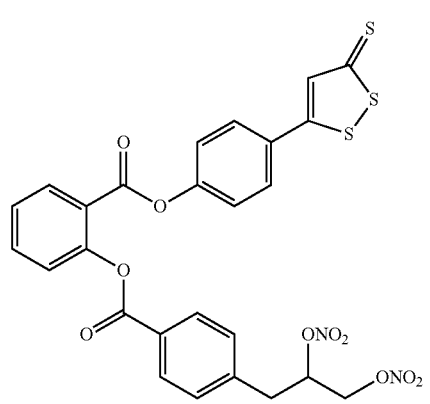
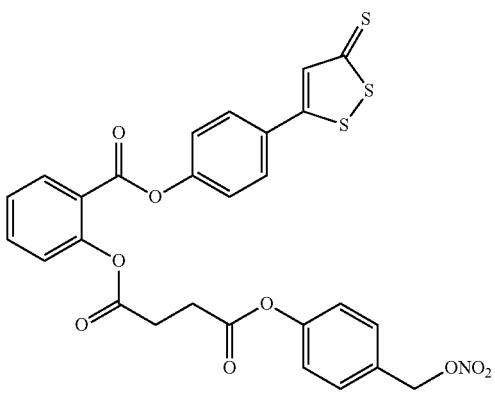

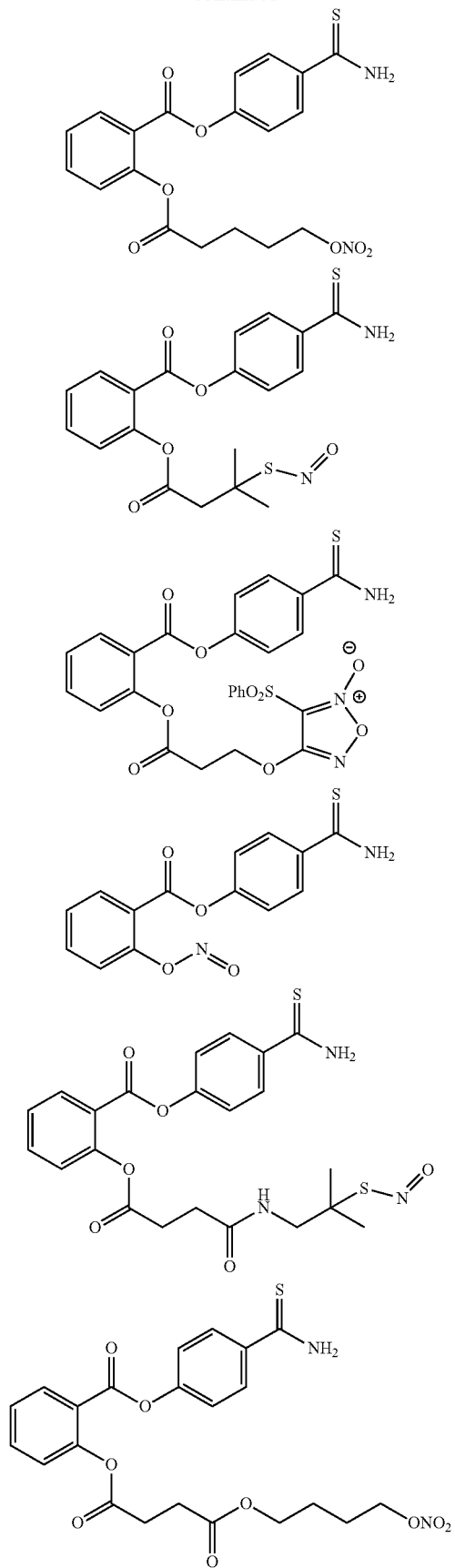
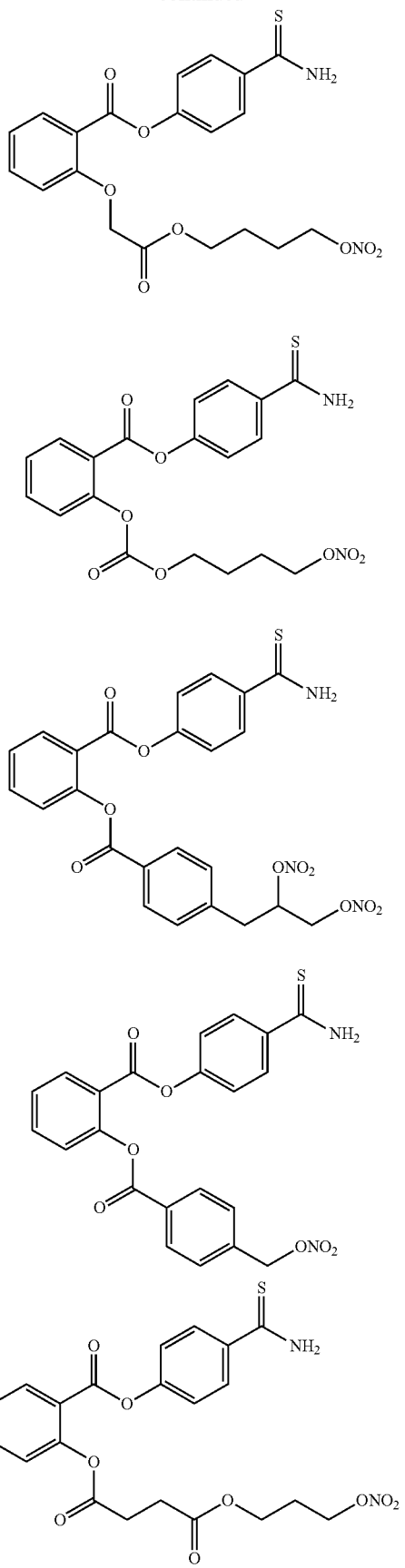

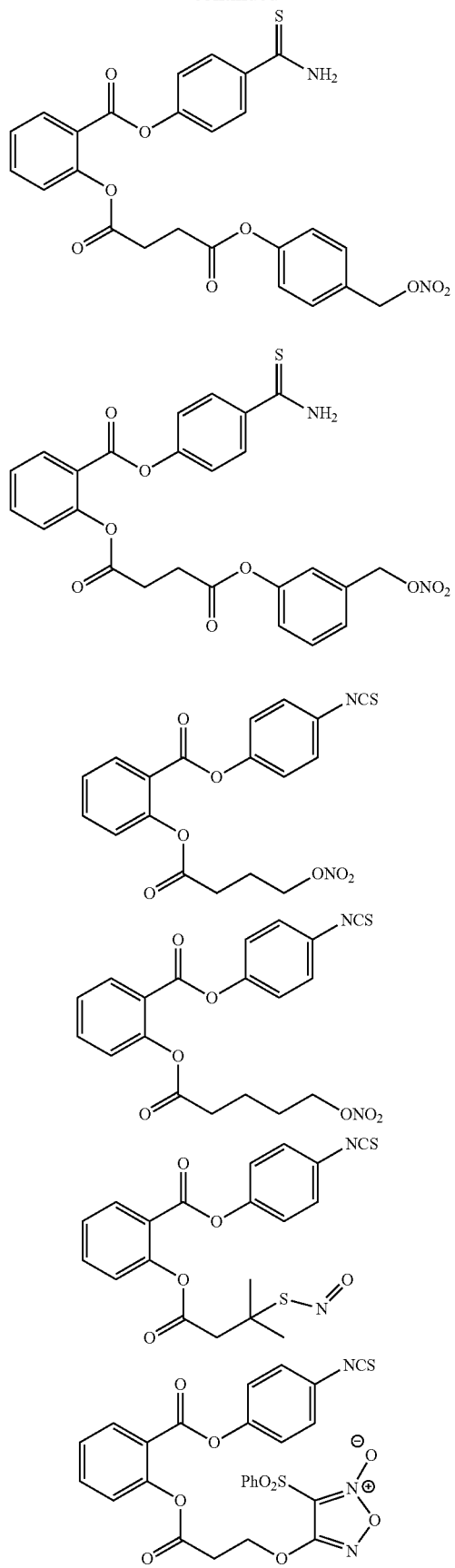
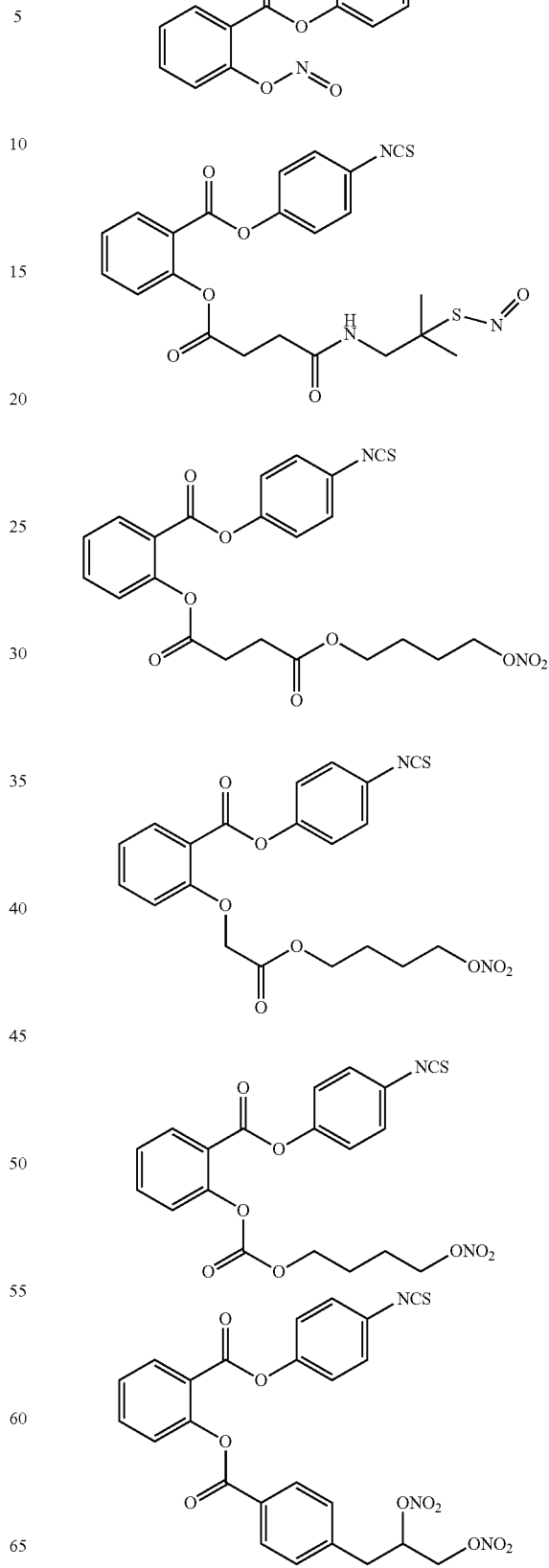

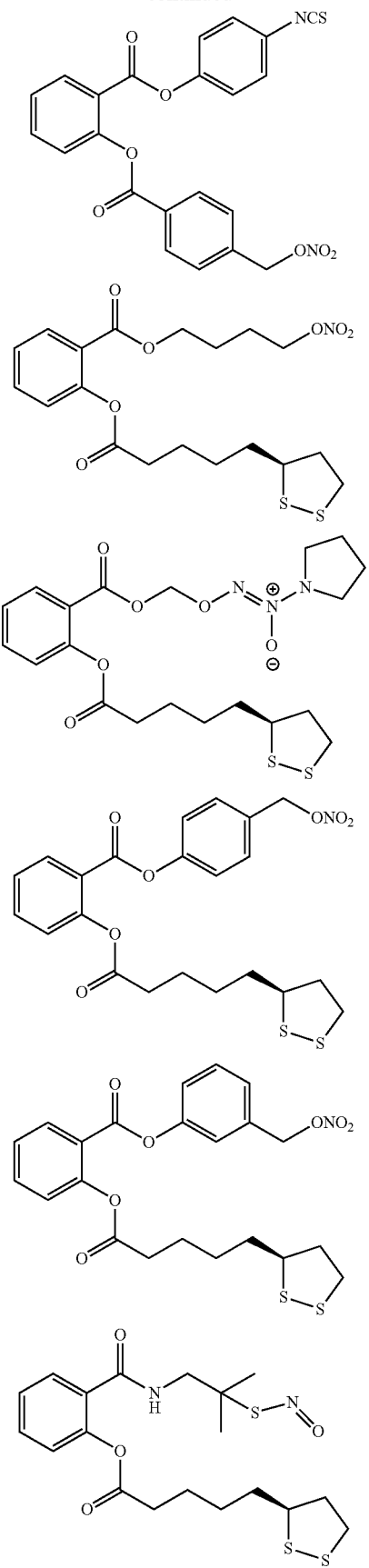
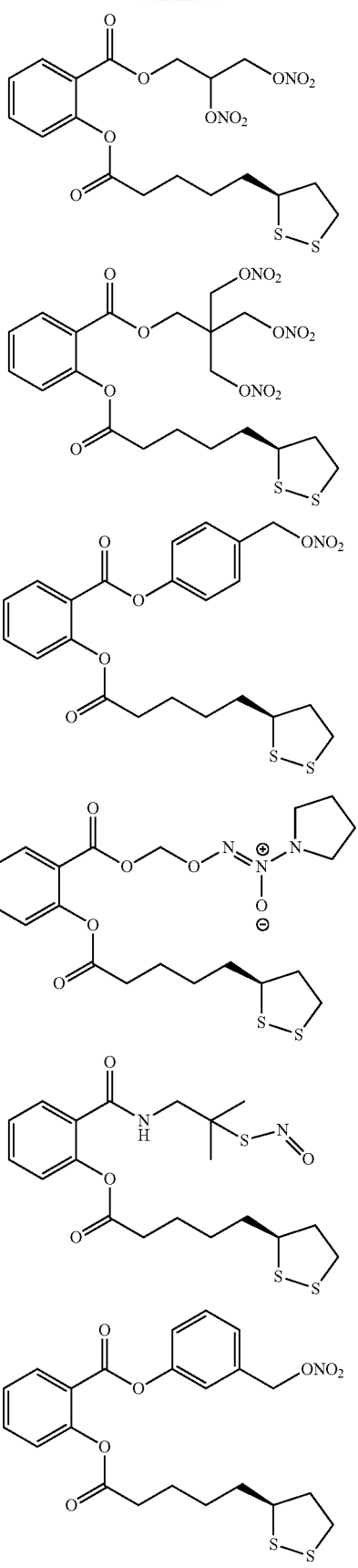

-continued
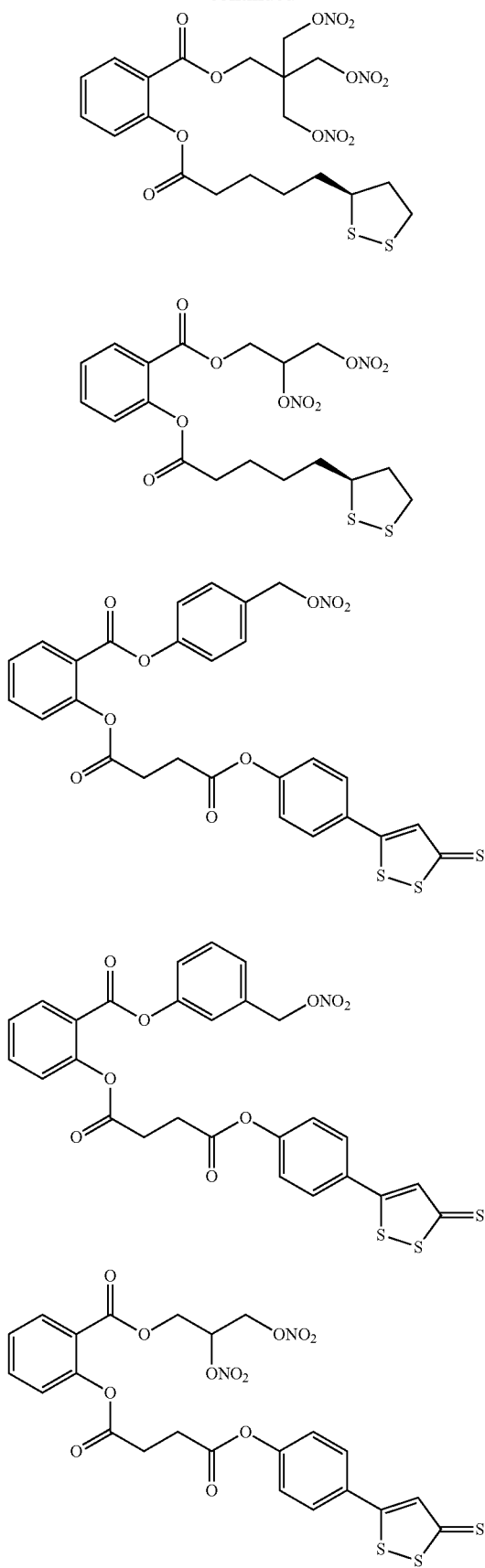
-continued
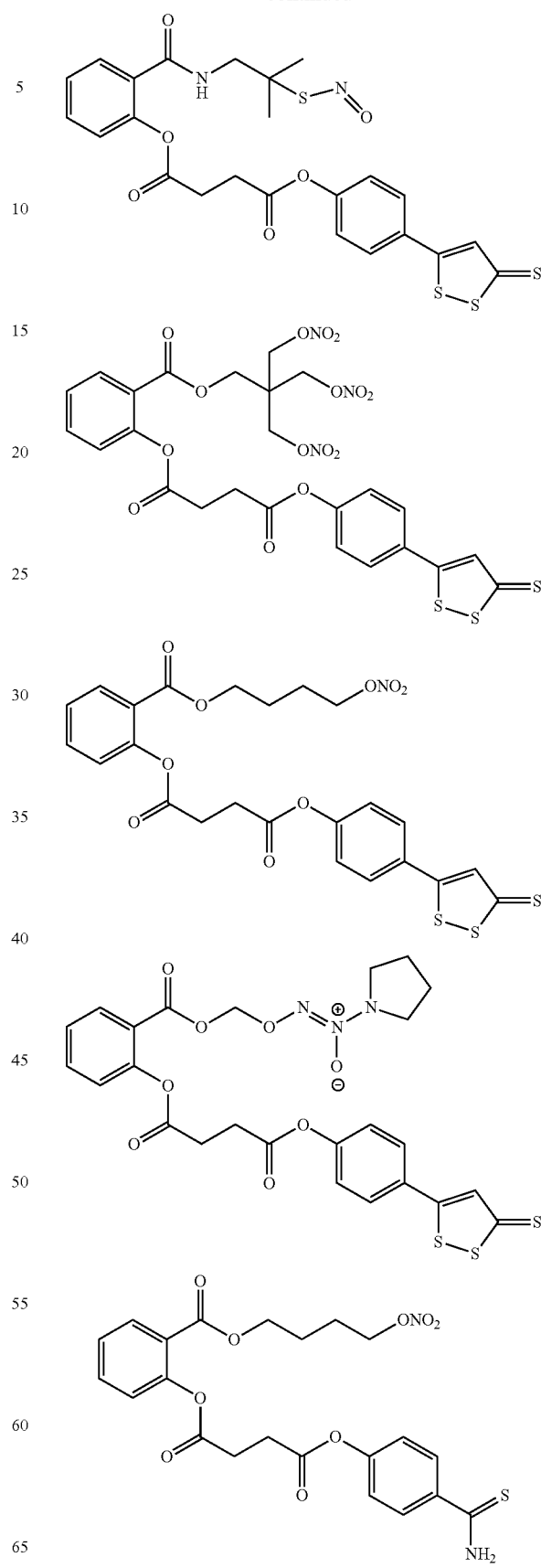

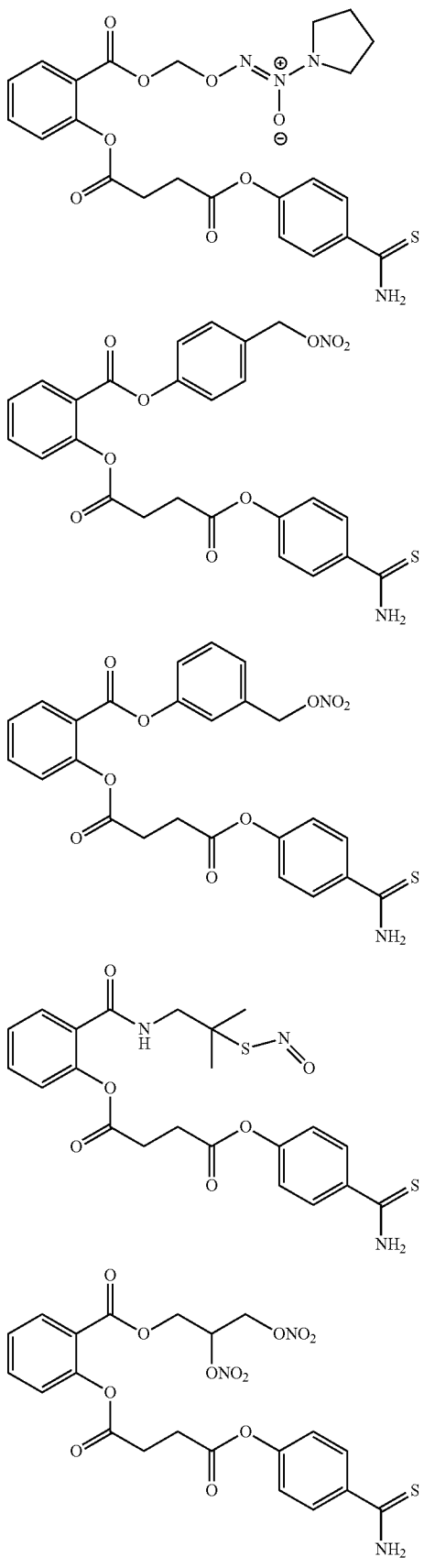

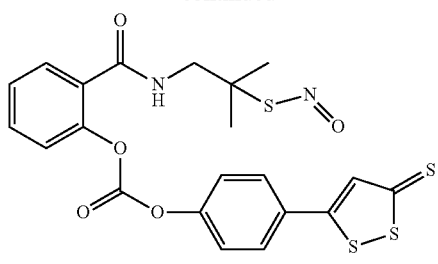
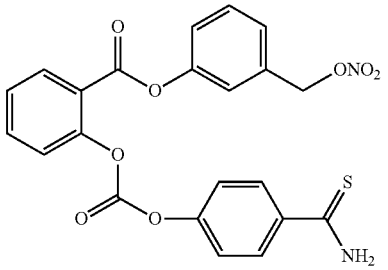
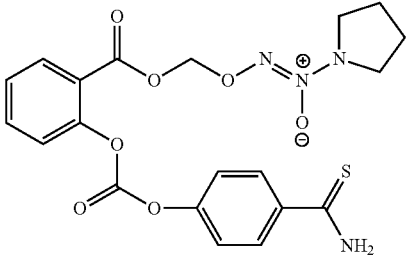
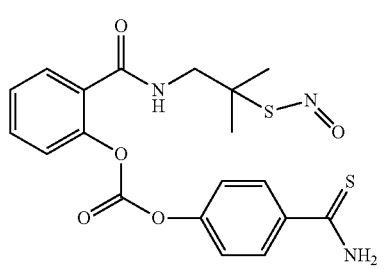
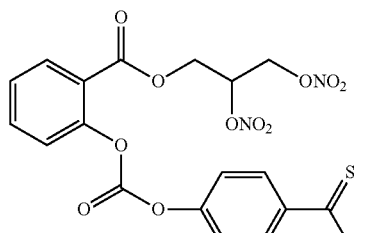
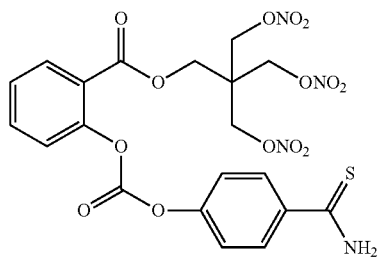
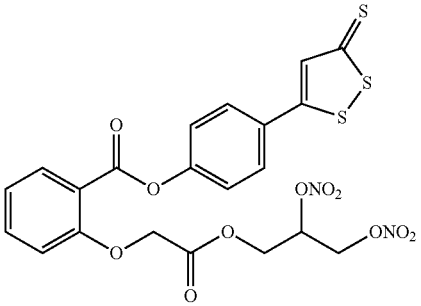

-continued
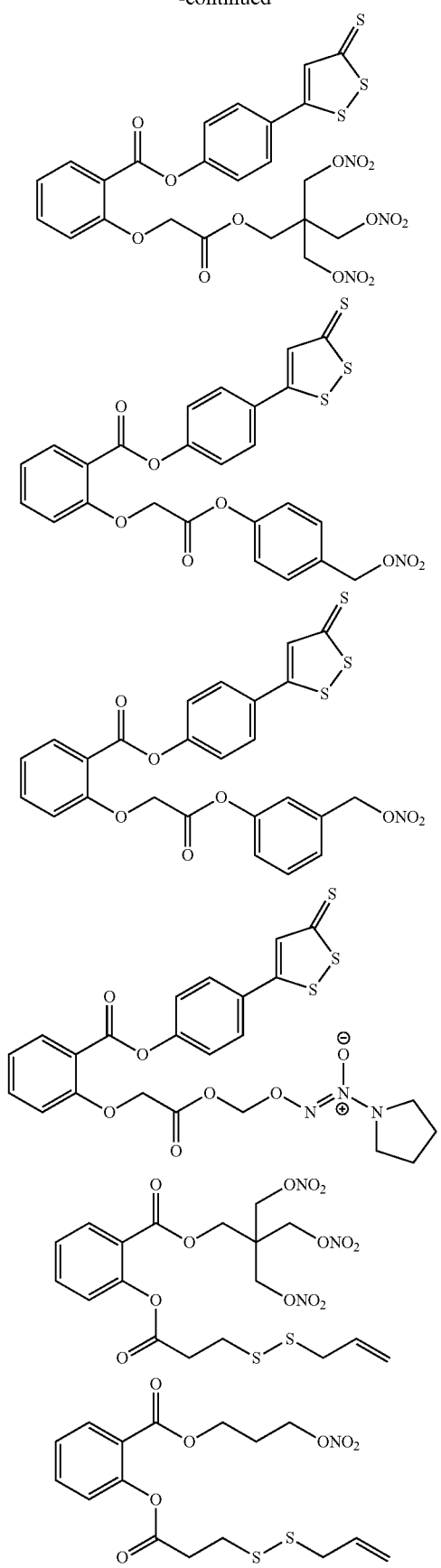
-continued
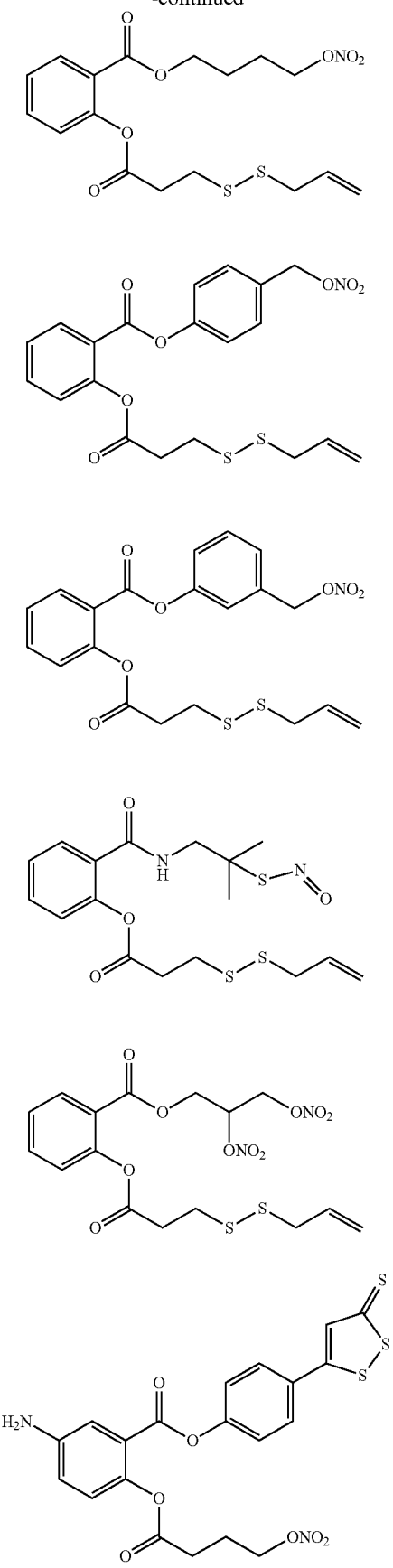

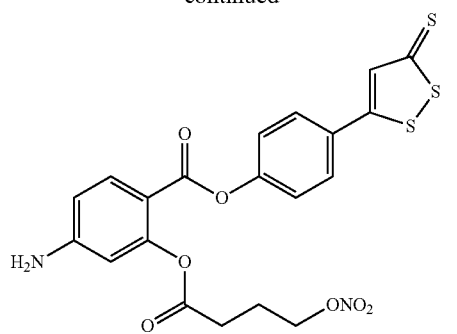
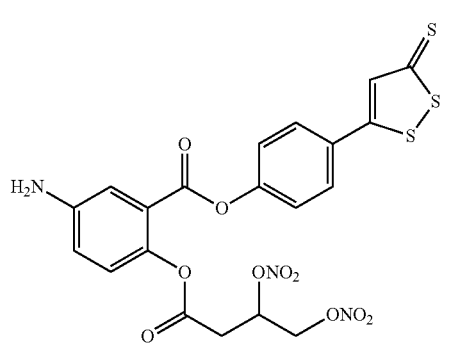
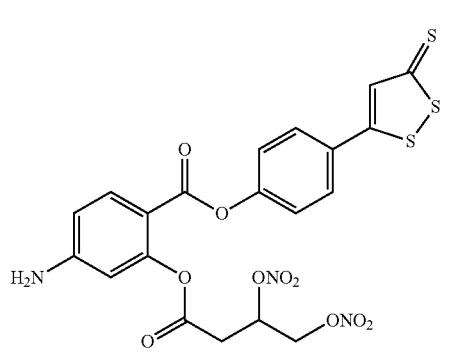
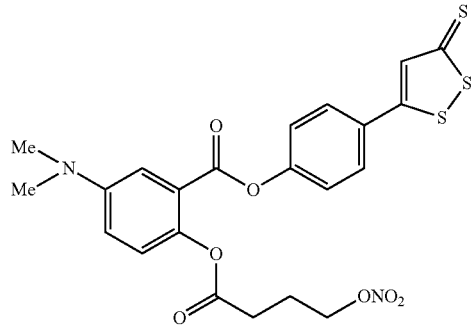
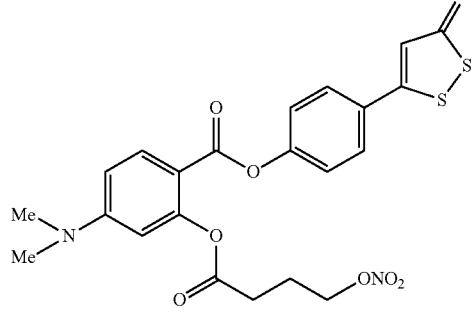
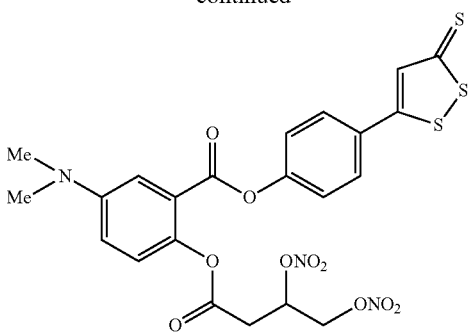
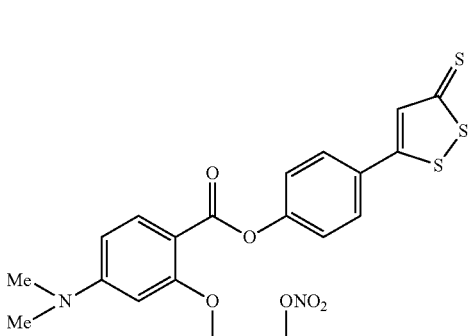
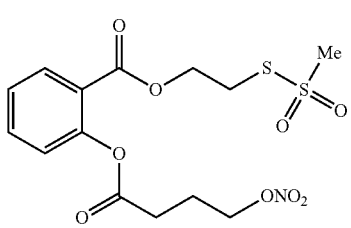
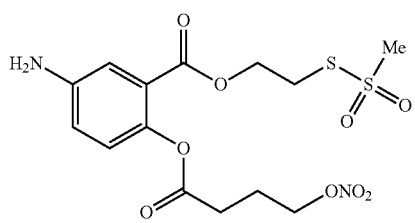
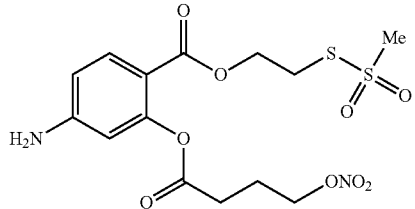
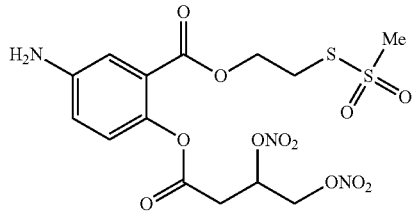

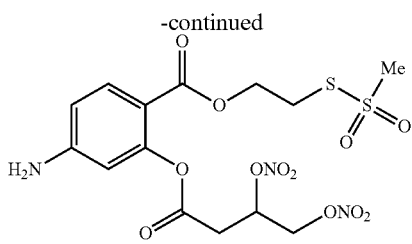

As used herein, "a NO-releasing moiety" refers to a moiety that can be cleaved from a parent compound to generate NO under physiological conditions after the parent compound is administered to a patient. Examples of suitable NO-releasing moieties include —NO, —C(O)—(CH$_2$)$_n$—ONO$_2$, —O—(CH$_2$)$_n$—ONO$_2$, —(CH$_2$)$_n$—ONO$_2$, —C(O)—CH$_2$—C(CH$_3$)$_2$—SNO, —NH—CH$_2$—C(CH$_3$)$_2$—SNO, —CH$_2$—C(CH$_3$)$_2$—SNO,

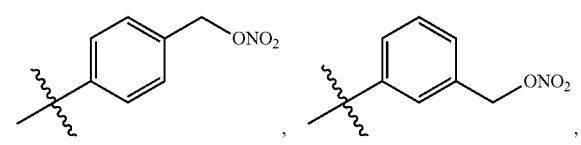

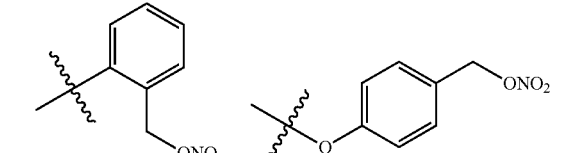

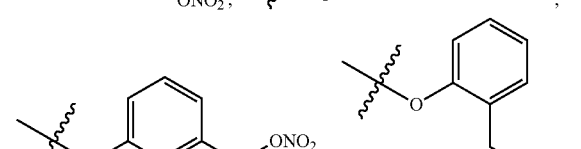

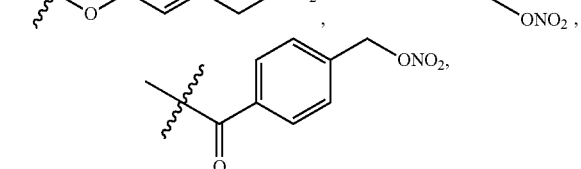

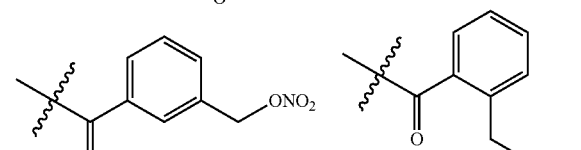

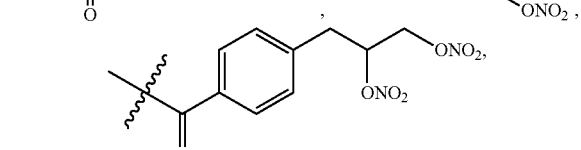

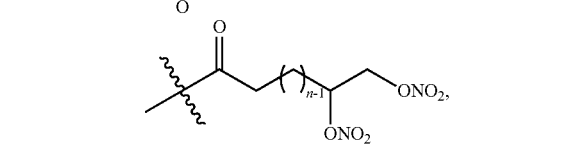

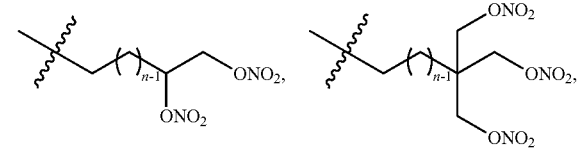

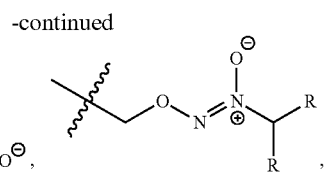

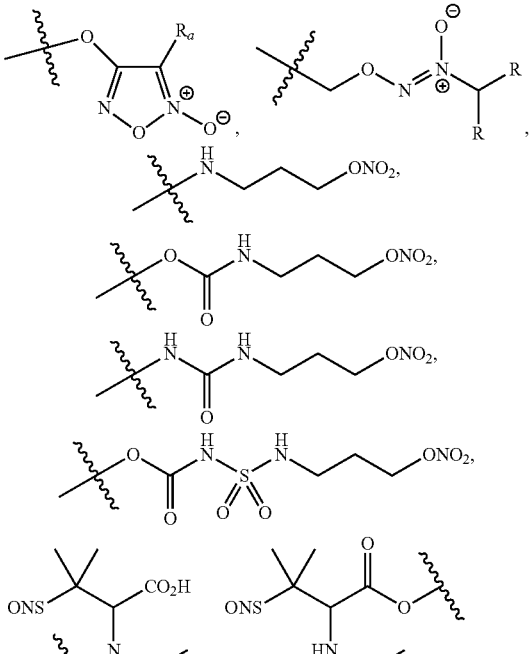

, and

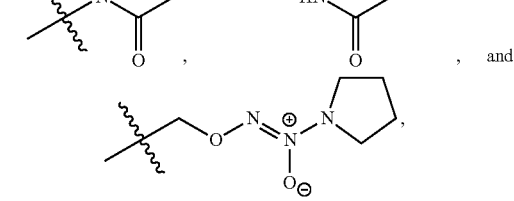

in which n is 1, 2, 3, 4, 5, 6, or 7; R$_a$ is H, C$_1$-C$_{10}$ alkyl, aryl, S(O)$_2$-aryl, CN, or CON(R$_b$)$_2$; and each R$_b$, independently, is H or C$_1$-C$_{10}$ alkyl.

The term "alkyl" refers to a saturated, linear or branched hydrocarbon moiety, such as —CH$_3$ or —CH(CH$_3$)$_2$. The term "aryl" refers to a hydrocarbon moiety having one or more aromatic rings. Examples of aryl moieties include phenyl (Ph), naphthyl, pyrenyl, anthryl, and phenanthryl. Alkyl and aryl mentioned herein include both substituted and unsubstituted moieties, unless specified otherwise. Possible substituents on aryl include, but are not limited to, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, C$_1$-C$_{10}$ alkoxy, aryl, aryloxy, heteroaryl, heteroaryloxy, amino, C$_1$-C$_{10}$ alkylamino, C$_1$-C$_{20}$ dialkylamino, arylamino, diarylamino, C$_1$-C$_{10}$ alkylsulfonamino, arylsulfonamino, C$_1$-C$_{10}$ alkylimino, arylimino, C$_1$-C$_{10}$ alkylsulfonimino, arylsulfonimino, hydroxyl, halo, thio, C$_1$-C$_{10}$ alkylthio, arylthio, C$_1$-C$_{10}$ alkylsulfonyl, arylsulfonyl, arylsulfonamide, heteroarylsulfonamide, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl include all of the above-recited substituents except C$_1$-C$_{10}$ alkyl.

As used herein, "a H$_2$S-releasing moiety" refers to a moiety that can be cleaved from a parent compound to generate H$_2$S under physiological conditions after the parent compound is administered to a patient. Examples of suitable H$_2$S-releasing moieties include:

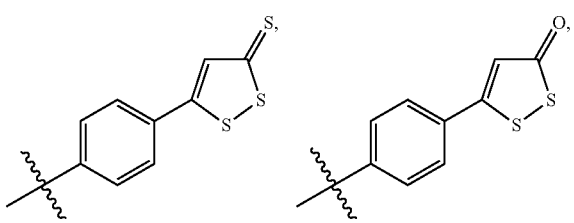
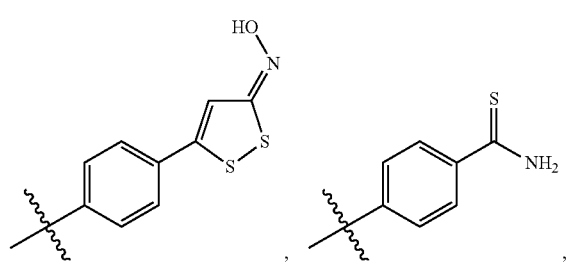
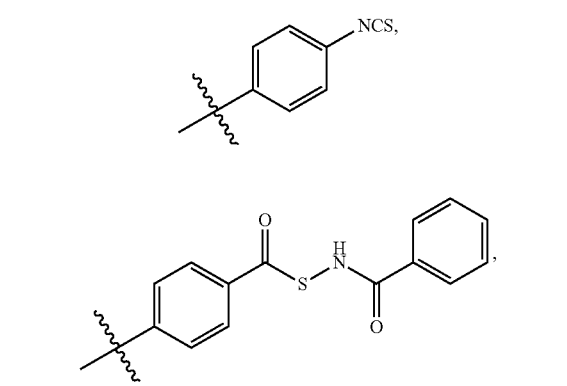
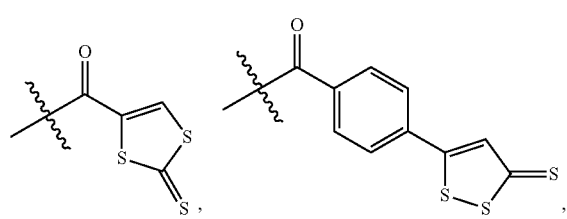
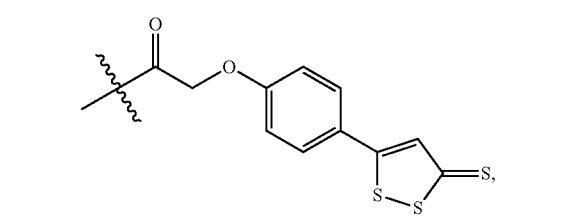
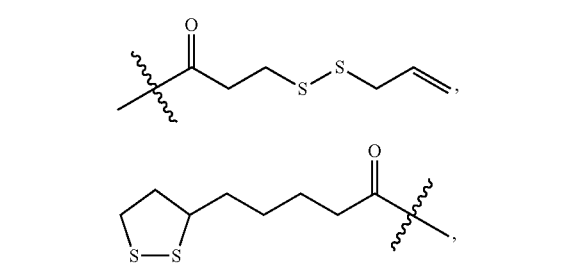

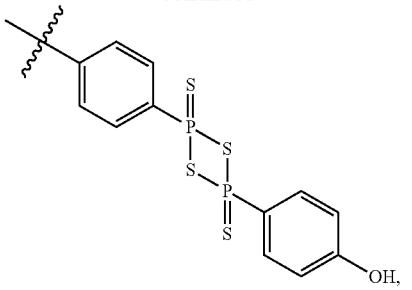
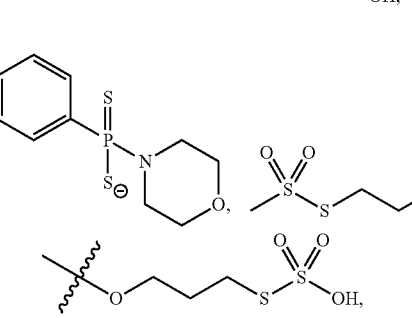
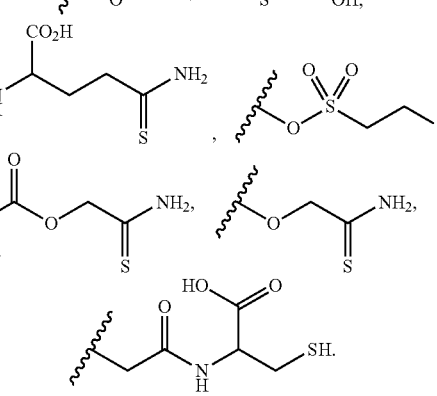

In another embodiment of the invention, the compound may be NOSH, an NO-releasing moiety and an $H_2S$-releasing moiety without an NSAID-derived core. The structure of NOSH is shown below:

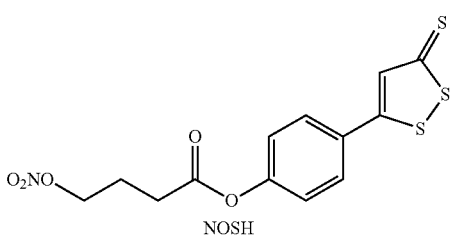

NOSH

The compounds of the invention may be synthesized by known methods in the art. For example, see International Patent Publication No. WO 2013/025790, which discusses synthesis of the compounds.

The compounds can be administered to the plants by any known method in the art. For example, the compounds may be dissolved in water and the solution may be sprayed on the plants or poured onto the soil covering the roots of the plants. The solution may also be added to an irrigation system.

An appropriate dosage of compound can be readily determined by a person having skill in the art. Dosage may vary depending upon the species of plant, the size of the plant, and the general health of the plant. For example, the minimum dosage per plant per day may be about 50 mg, 75 mg, or 100 mg. The maximum dosage per plant per day may be about 300 mg, 400 mg, 500 mg, or 600 mg per plant per day. A single dosage may be dissolved in 1 or more gallons of water and administered to the plant.

Alternatively, the dosage may be dissolved in a solvent and administered to the plant by foliar spraying. Foliar spraying involves feeding the plant by applying the composition and dosage directly to the leaves of the plant. The choice of solvent and dosage can be determined by a person having skill in the art. Water and methanol are preferred solvents. Certain solvents must be avoided because they cause toxicity in some plants.

Any dosage can be used that does not adversely affect the plant. Dosages can easily be determined by trial and error as each type of plant may have different needs. For example, a minimum dosage may be about 10 µM, 20 µM, 30 µM, or 50 µM. Likewise, for example, the maximum dosage may be about 150 µM, 200 µM, or 300 µM. A preferred dosage may be about 100 µM.

Cellular damage in leaves can be measured by determining lipid peroxidation (Malondialdehyde [MDA] content) and hydrogen peroxide ($H_2O_2$) levels. Lipid peroxidation is a widely used stress indicator of plant membranes. For example, the method described by Heath and Packer is the basic protocol used or adapted in numerous studies dealing with lipid peroxidation. See Heath R L, Packer L. 1968, Photoperoxidation in isolated chloroplasts. I. Kinetics and stoichiometry of fatty acid peroxidation. Archives in Biochemistry and Biophysics 125, 189-198. Measuring hydrogen peroxide levels is also well known in the art.

In another embodiment, the invention relates to a method of priming a plant against abiotic stress factors comprising treating the plant with a composition comprising a compound containing an NO-releasing moiety and an $H_2S$-releasing moiety covalently bonded to an aspirin derived core or NOSH, as described above. Priming the plant includes administering the compound to a plant so it may better withstand abiotic stress factors such as drought, salinity, and heat.

In yet another embodiment, the invention relates to a method of promoting plant growth comprising treating the plant with a composition comprising a compound containing an NO-releasing moiety and an $H_2S$-releasing moiety covalently bonded to an aspirin derived core or NOSH, as described above. Promoting plant growth may involve greener leaves, healthier leaves, bigger leaves, more leaves, overall increased weight, and/or faster growth compared to control plants.

The plant may be treated by any method known in the art. For example, treatment of the plant may begin at the seedling stage where the seeds may be coated with a composition containing the compound. Compositions may be formulated so that the compound is released slowly to the seed throughout the germination process. The plant may also be treated after germination of the seed by traditional methods by which plant food and fertilizers are administered such as by foliar spraying or by administration of the compound directly to the soil or during watering.

EXAMPLES

Example 1

The present study shows the ameliorative effect of NOSH-aspirin application on *Medicago truncatula* plants subjected to drought stress conditions, whereby cellular damage was significantly lowered, as was hydrogen peroxide content, after application of the priming agent, thus highlighting a novel function-use for this compound.

Plant Material and Stress Conditions

Mature (40 d) *Medicago truncatula* ecotype Jemalong A17 plants were used for the purposes of this study. These were grown in soil medium under controlled, optimal growth conditions and were then subjected to drought stress. Drought was imposed by withholding watering for 9 d (for detailed growth and stress conditions see Filippou et al., 2011). Both NOSH and NOSH-aspirin were applied at 100 µM concentration by foliar spraying at the start of stress imposition. The hybrid donors were diluted in 70% (v/v) and 30% (v/v) methanol, 20% (v/v) acetone or 20% (v/v) DMSO. Cellular damage was evaluated by lipid peroxidation levels (TBARS content) and hydrogen peroxide ($H_2O_2$) content as previously described (Filippou et al., 2011; Tanou et al., 2012), while osmoprotective capacity was evaluated by proline content (ninhydrin assay) as previously described (Antoniou et al., 2013). Real-time RT-PCR gene expression analysis was carried out using a Biorad IQ5 thermocycler as previously described (Filippou et al., 2013b). Relative quantification of gene expression and statistical analysis of all qRT-PCR data (pairwise fixed reallocation randomization test) were performed using the REST software according to Pfaffl et al. (2002). The actin 11 gene was used as a housekeeping reference gene. All analyses were carried out using three independent biological pools of samples as replicates (with a minimum of three independent plants per pooled sample).

Results and Discussion

Cellular Damage

An examination of cellular damage levels was performed by means of spectrophotometric determination of lipid peroxidation. Significant membrane damage was observed under drought conditions; however, MDA content was lowered following NOSH and NOSH-aspirin (NOSH-A) pre-treatment diluted in 70% (v/v) MetOH, with NOSH-aspirin providing statistically significant protection in comparison with control samples (FIG. 1).

Figure 2:
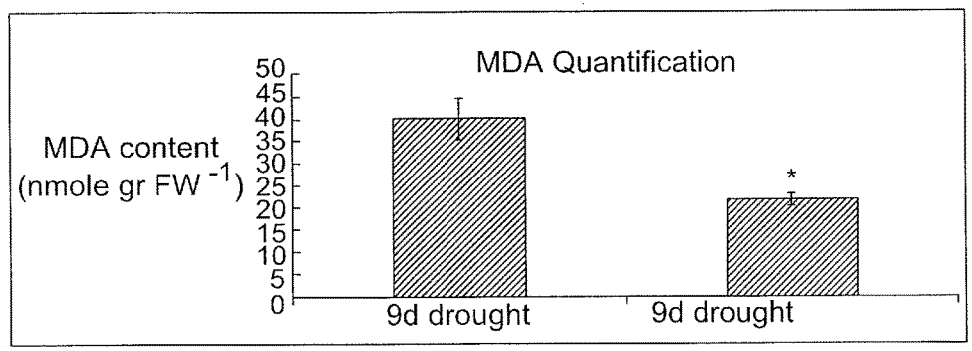
FIG. 2 Cellular damage indicated by leaf MDA content in drought-stressed *M. truncatula* plants in the presence or absence of NOSH-aspirin pre-treatment dissolved in 30% (v/v) MetOH (n=3).

The experiment was repeated using 30% (v/v) MetOH as a solvent, where the protective effect of NOSH-A pre-treatment was observed once more, with primed plants showing significantly lower lipid peroxidation levels compared with drought-stressed, control samples (FIG. 2).

Figure 3A:
FIG. 3 Toxicity symptoms (manifested as chlorosis) resulting from treatment with 20% acetone (a) or 20% DMSO (b) in leaves of *M. truncatula* plants.
Figure 3B:
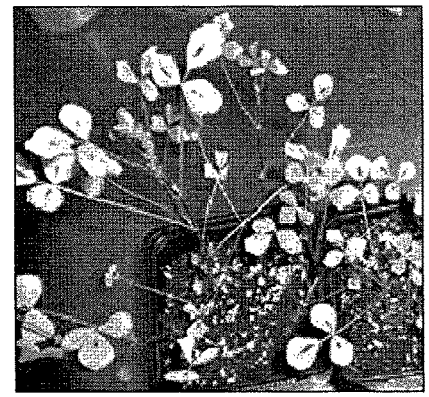

Further attempts were made to examine the efficiency of other solvents for NOSH-A; these included 20% DMSO and 20% acetone. However, treatment with the solvent itself resulted in toxicity symptoms (extensive chlorosis; see FIG. 3) although protection in NOSH-A pre-treated plants was still evident from lower lipid peroxidation levels; therefore, these solvents were avoided for further studies and MetOH was chosen as an optimal solvent for the donor.

Reactive Oxygen Species Content

Figure 4:
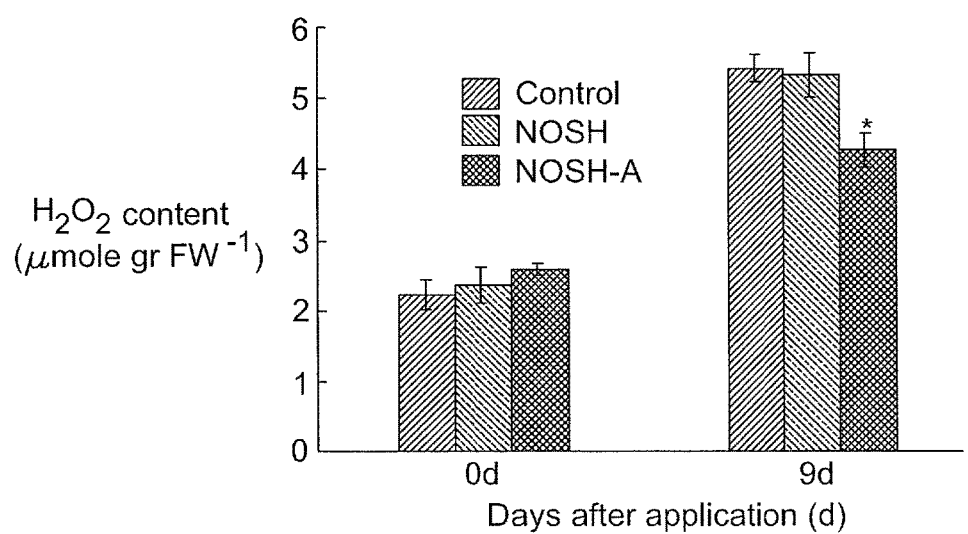
FIG. 4 Hydrogen peroxide content in leaves of drought-stressed *M. truncatula* plants in the presence or absence of NOSH/NOSH-aspirin pre-treatment (dissolved in 70% (v/v) MetOH) (n=3).

Abiotic stress conditions are associated with increased levels of reactive oxygen species (ROS), which are toxic for the cells. During such conditions, the production of ROS exceeds the capacity of the antioxidative systems to remove them, causing oxidative stress. Quantification of $H_2O_2$ (major ROS) content revealed a massive induction in drought-stressed plants, which was significantly reversed in NOSH-aspirin (dissolved in 70% (v/v) MetOH) pre-treated plants compared with control samples (FIG. 4).

Figure 5:
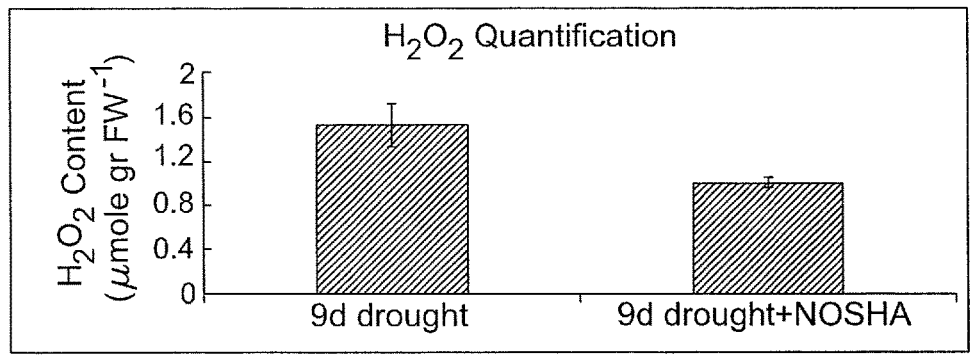
FIG. 5 Hydrogen peroxide content in leaves of drought-stressed *M. truncatula* plants in the presence or absence of NOSH-aspirin pre-treatment (dissolved in 30% (v/v) MetOH) (n=3).

Similarly, NOSH-A pre-treated plants prior to drought stress imposition showed significantly lower $H_2O_2$ levels compared with drought-stress samples when using 30% (v/v) MetOH (FIG. 5).

Figure 6:
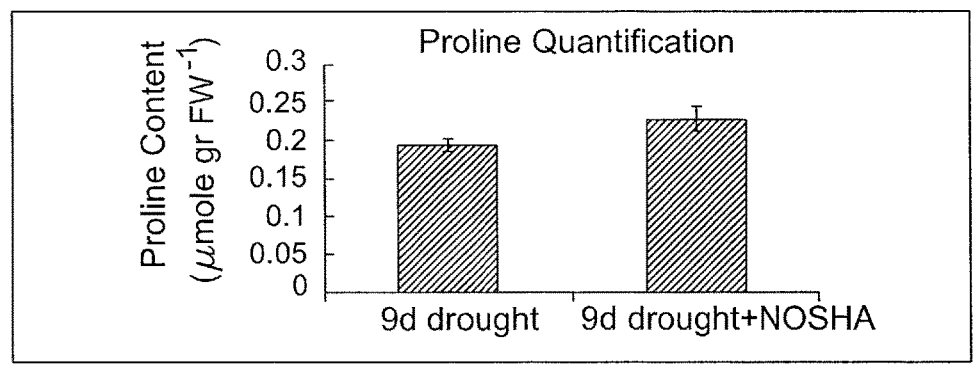
FIG. 6 Proline content in leaves of drought-stressed *M. truncatula* plants in the presence or absence of NOSH-A pre-treatment (dissolved in 30% (v/v) MetOH) (n=3).

In addition, proline content was evaluated as proline is a major osmoprotective molecule involved in the defense response of plants to abiotic stress conditions (Filippou et al., 2013b). Results showed that pre-treatment of plants with NOSH-A (dissolved in 30% (v/v) MetOH) prior to drought stress imposition resulted in increased proline content compared with drought-stressed alone samples (FIG. 6).

Figure 7:
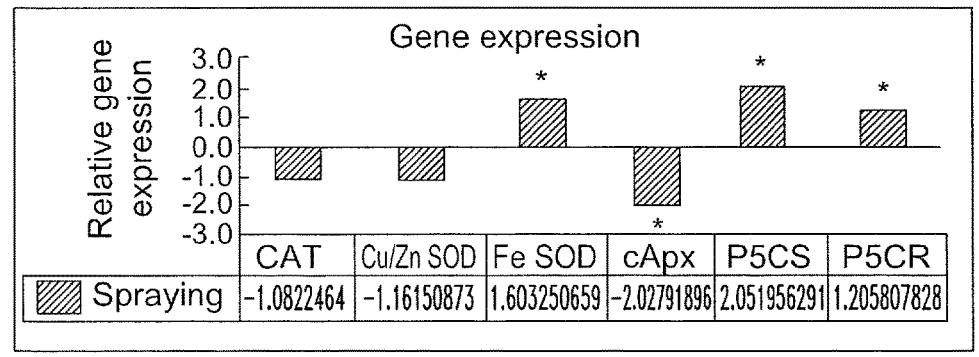
FIG. 7 Real-time RT-PCR relative gene expression levels in leaves of NOSH-A (dissolved in 30% (v/v) MetOH) pre-treated, drought-stressed *M. truncatula* plants compared with drought-stressed samples). CAT=catalase, Cu/ZnSOD=Cu/Zn superoxide dismutase, FeSOD=Fe superoxide dismutase, cAPX=cytosolic ascorbate peroxidase, P5CS and P5CR are major enzymes involved in proline biosynthesis.

Finally, qRT-PCR gene expression analysis was carried out for key defense-related genes, including major enzymatic antioxidants (CAT, Cu/ZnSOD, FeSOD, cAPX), as well as genes involved in proline biosynthesis (P5CS, P5CR). Interestingly, NOSH-A pre-treated plants demonstrated significant transcriptional regulation for most of the genes examined, with FeSOD, P5CS and P5CR showing significant induction in pre-treated and subsequently stressed plants compared with stressed alone plants, while cAPX showed significant suppression (FIG. 7). The induction in the proline biosynthetic enzyme gene expression levels comes in support of the observed increased proline content, while the induction in FeSOD transcripts is in agreement with a recent report by Fotopoulos et al. (2014), who demonstrated that treatment with 100 μM of NO donor sodium nitroprusside results in significant induction of FeSOD in mature *Medicago truncatula* plants.

The current findings show NOSH-aspirin's capacity to provide significant protection in *Medicago truncatula* plants against drought stress conditions, which result in major cellular damage in controls plants.

Example 2

A new, large pharmacological approach experiment has been carried out, where a variety of treatments and combinations thereof were applied. The treatments were as follows:

| | |
|---|---|
| w-m | Control (methanol) |
| D-m | Drought (methanol) |
| D-w | Drought ($H_2O$) |
| D-N | Drought NOSH |
| D-NC | Drought-NOSH-cPTIO |
| D-NH | Drought-NOSH-HXL |
| D-NCH | Drought-NOSH-cPTIO-HXL |
| D-NA | Drought NOSHA |
| D-NAC | Drought-NOSHA-cPTIO |
| D-NAH | Drought-NOSHA-HXL |
| D-NACH | Drought-NOSHA-cPTIO-HXL | where cPTIO represents a NO inhibitor, while HXL is a $H_2S$ inhibitor. In addition to the previous setup of sampling control and drought-stressed samples, plants were re-watered at 6 d after drought stress imposition and additional sampling was carried out 1 d after rewatering to examine recovery of plants, while a second wave of drought stress was imposed to see if primed plants develop a longer-term, 'memory' effect.

Plant Material and Stress Conditions

Figure 8:
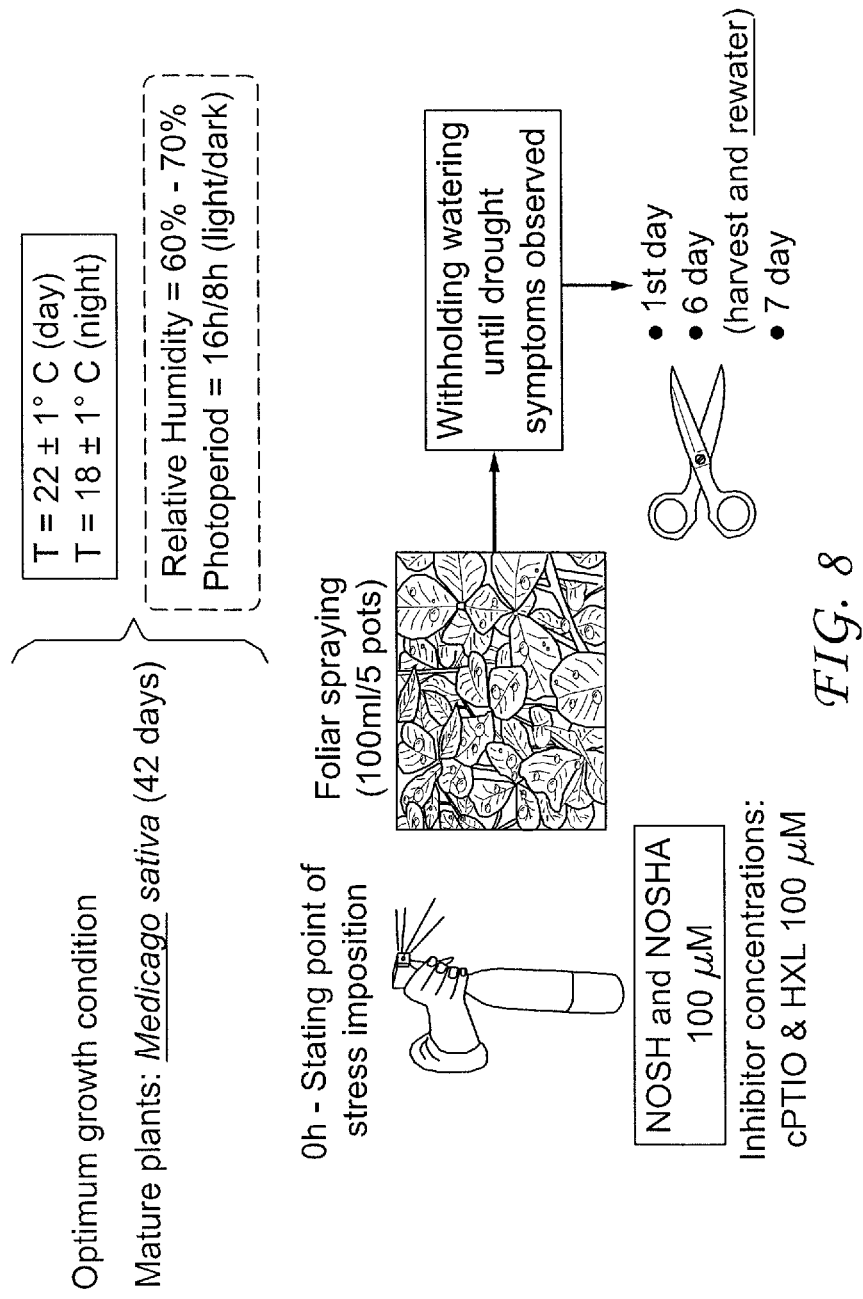
FIG. 8 Schematic representation of experimental setup.

Mature (42 d) *Medicago sativa* plants were used for the purposes of this study. These were grown in soil medium under controlled, optimal growth conditions and were then subjected to drought stress. Drought was imposed by withholding watering until drought symptoms (loss of turgour, wilting, chlorosis) were observed (6 d after stress imposition). Samples were then re-watered to observe recovery potential after 1 day (7 d). Both NOSH and NOSH-aspirin were applied at 100 μM concentration by foliar spraying at the start of stress imposition. The hybrid donors were diluted in 30% (v/v) methanol. Physiological parameters (stomatal conductance and chlorophyll fluorescence) were measured with a DT-Porometer AP4 (Delta-TDevices, Cambridge, UK) and an OptiSci OS-30p chlorophyll fluorometer (Opti-Sciences, Hudson, N.H., USA) respectively (Filippou et al., 2013). Chlorophyll fluorescence (Fv/Fm) of leaves represents the maximum photochemical efficiency of photosystem II (PSII). Cellular damage was evaluated by lipid peroxidation levels (TBARS content), nitric oxide (NO) content (nitrosative stress) and hydrogen peroxide ($H_2O_2$) content (oxidative stress) as previously described (Filippou et al., 2011; Tanou et al., 2012), while osmoprotective capacity was evaluated by proline content (ninhydrin assay) as previously described (Antoniou et al., 2013). Antioxidant enzyme activities (SOD and CAT) were measured as previously described (Filippou et al., 2014). Real-time RT-PCR gene expression analysis was carried out using a Biorad IQ5 thermocycler as previously described (Filippou et al., 2013). Relative quantification of gene expression and statistical analysis of all qRT-PCR data (pairwise fixed reallocation randomization test) were performed using the REST software according to Pfaffl et al. (2002). The actin 11 gene was used as a housekeeping reference gene. All analyses were carried out using three independent biological pools of samples as replicates (with a minimum of fifteen independent plants per pooled sample). The experimental setup is shown schematically in FIG. 8.

Results and Discussion

Phenotypes

Figure 9:
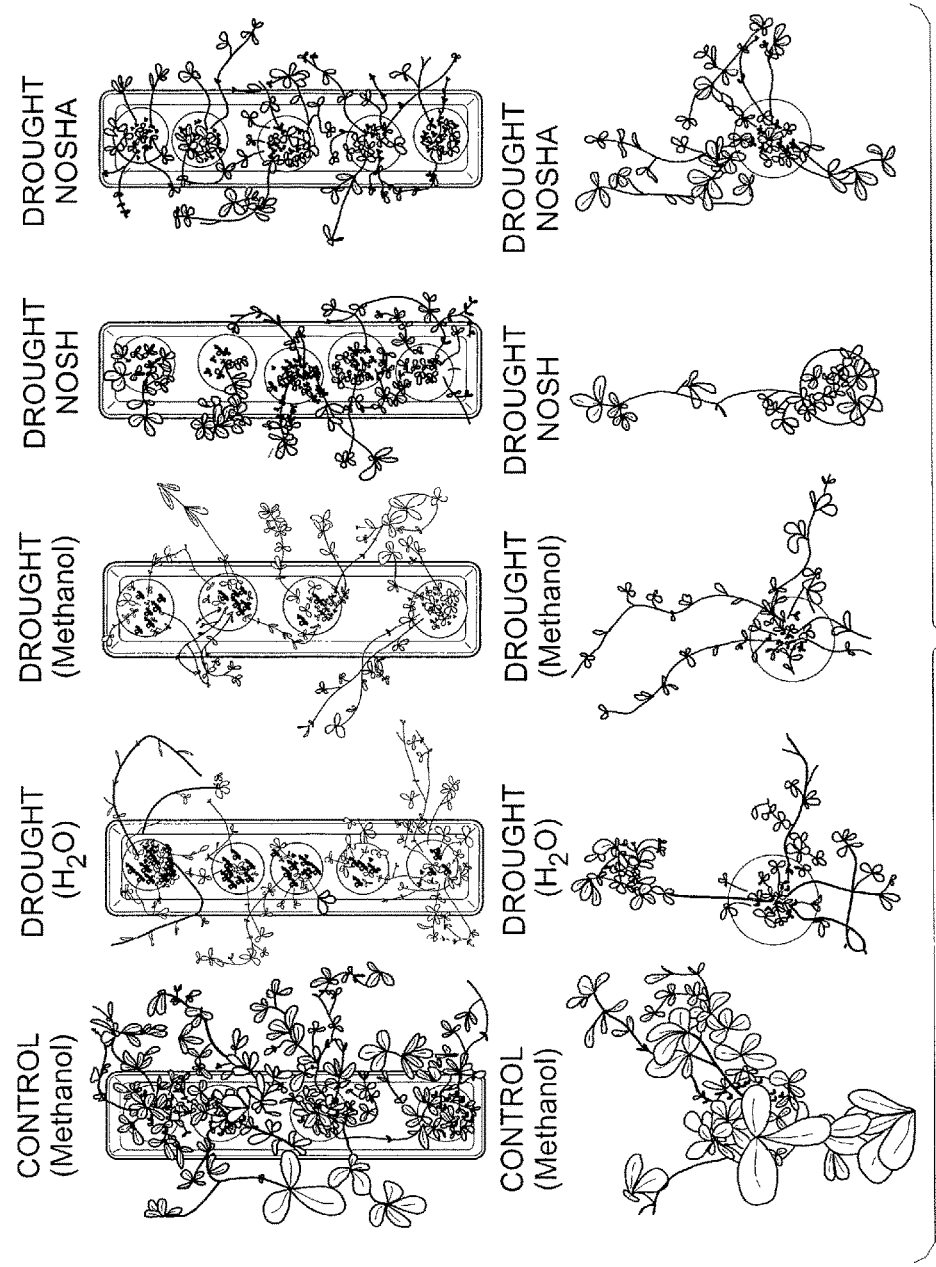
FIG. 9 Phenotypes of groups of samples at day 6 following drought stress imposition.

Macroscopic (phenotypic) observation of plants showed that NOSH and NOSH-A pretreated plants that were subsequently drought-stressed had significantly improved vitality, turgor and greening in comparison with drought-stressed plants which demonstrated extensive chlorosis and loss of turgor indicative of stress-related damage at 6 d after stress imposition (FIG. 9).

Figure 10:
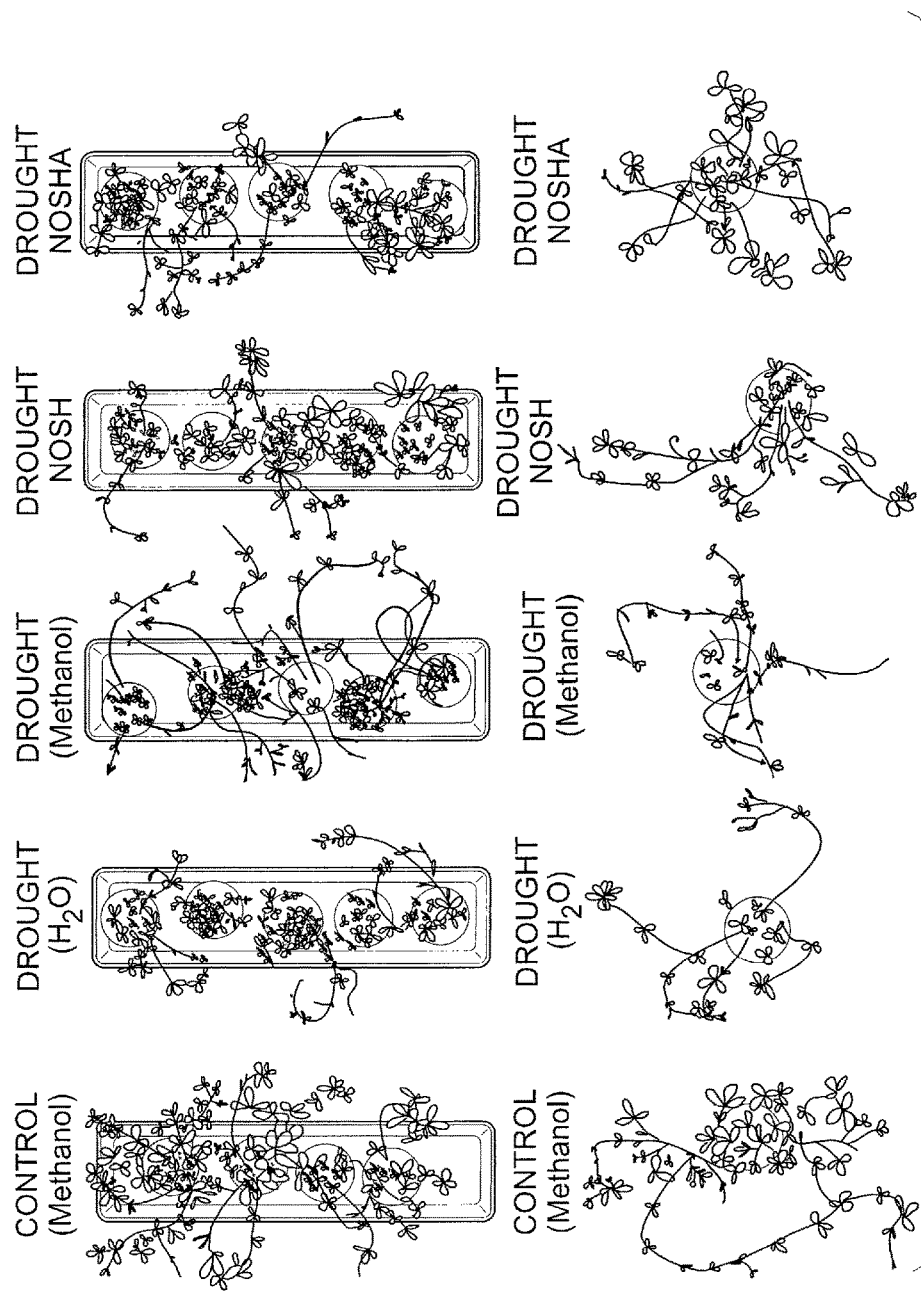
FIG. 10 Phenotypes of groups of samples at day 7 (6 d drought stress+1 d rewatering/recovery).

Rewatering for 1 d revealed that NOSH and NOSH-A pretreated samples had notably improved recovery capacity compared with drought-stressed alone samples, as pretreated plants retained turgor and greening while stressed-alone plants showed extensive chlorosis and initial signs of necrosis (FIG. 10).

Figure 11:
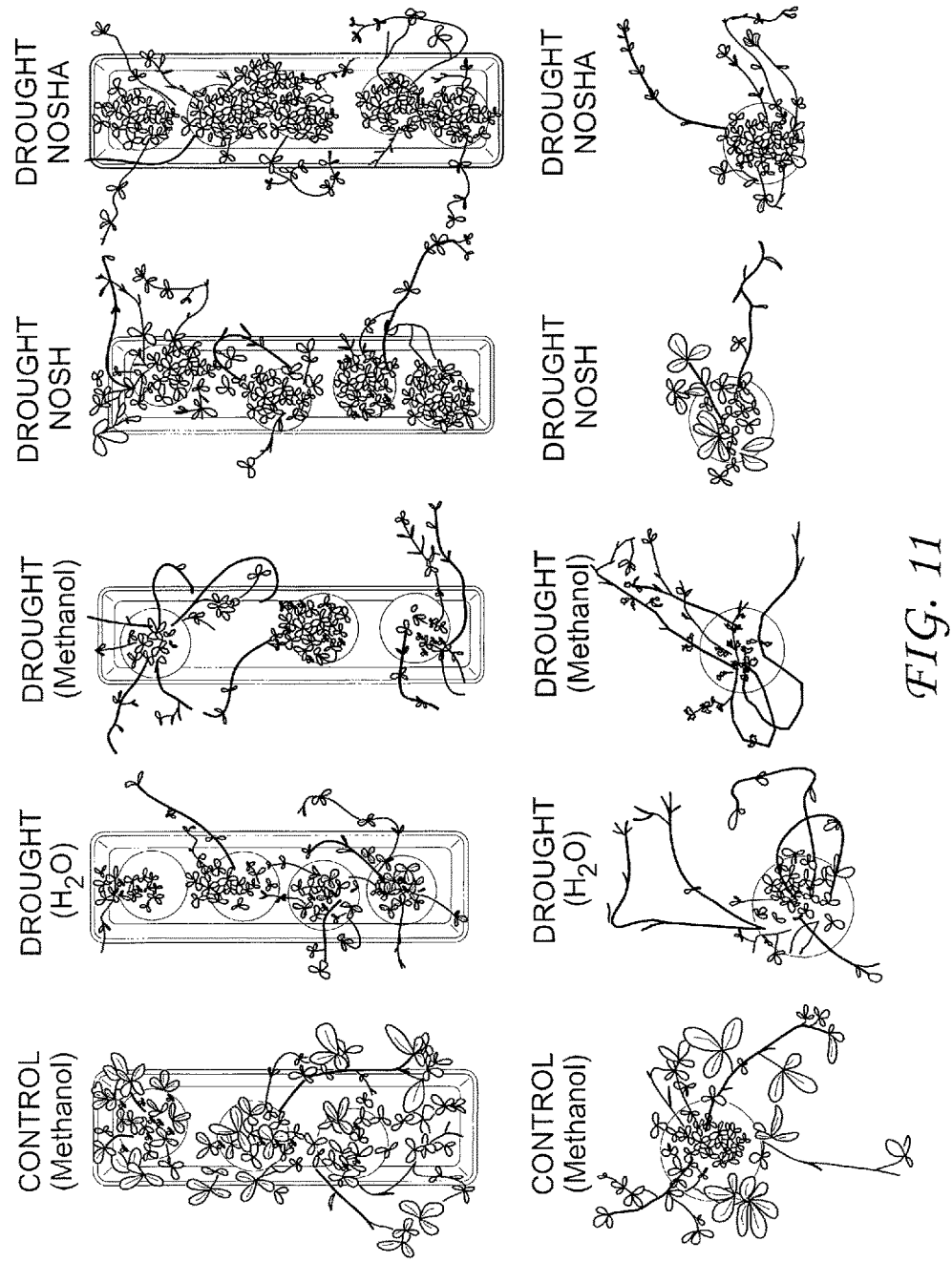
FIG. 11 Phenotypes of groups of samples at day 13 (following two waves of drought stress).

Interestingly, plants were left to grow following rewatering for another 6 days without any further watering on the basis of a second 'wave' of drought stress. Phenotypic observations revealed that NOSH and NOSH-A pretreated plants maintained growth and vitality, while drought-stressed alone plants showed extensive levels of tissue necrosis (FIG. 11).

Physiological Measurements

Measurements of physiological parameters indicative of the physiological state of the plant indicated that drought-stressed plants had significantly lower (stomatal conductance and chlorophyll fluorescence) levels compared with watered plants indicative of a stressed state, while NOSH and NOSH-A pretreated and subsequently stressed plants had ameliorated (significantly higher) stomatal conductance and chlorophyll levels compared with drought-stressed samples (FIG. 12).

Cellular Damage

Figure 13A:
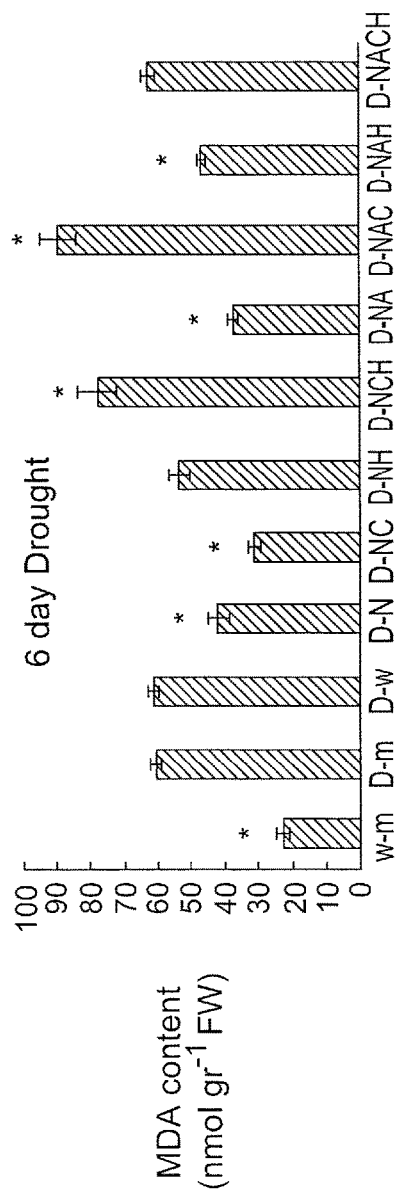
FIG. 13 Cellular damage indicated by leaf MDA content in *M. sativa* plants in the presence or absence of NOSH/NOSH-aspirin pretreatment.
Figure 13B:
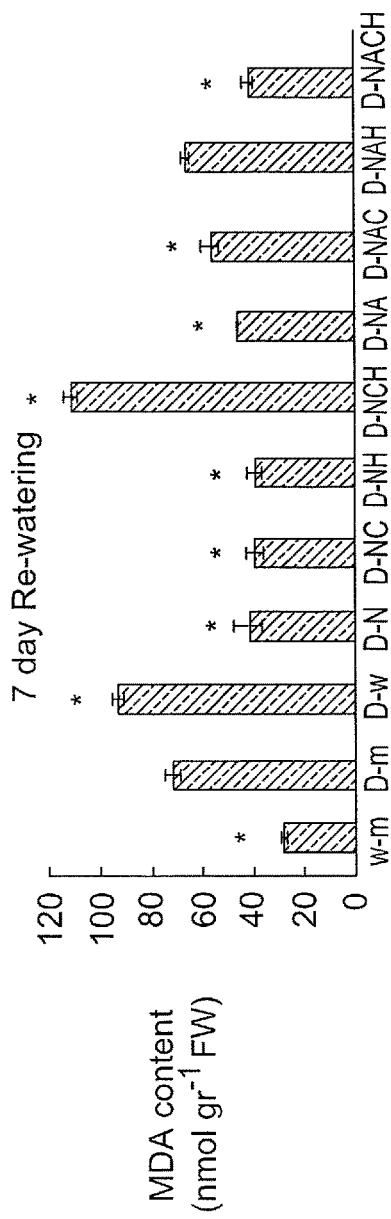

An examination of cellular damage levels was performed by means of spectrophotometric determination of lipid peroxidation. Significant membrane damage was observed under drought conditions; however, MDA content was lowered following NOSH and NOSH-aspirin pretreatment, with both NOSH and NOSH-aspirin providing statistically significant protection in comparison with drought-stressed samples (FIG. 13). In addition, rewatering could not ameliorate cellular damage in drought-stressed samples (showing further increase in MDA content at 7 d), whereas NOSH and NOSH-A pretreated samples maintained low MDA content levels close to those of control, watered samples (FIG. 13).

Reactive Oxygen and Nitrogen Species Content

Figures 1, 14B:
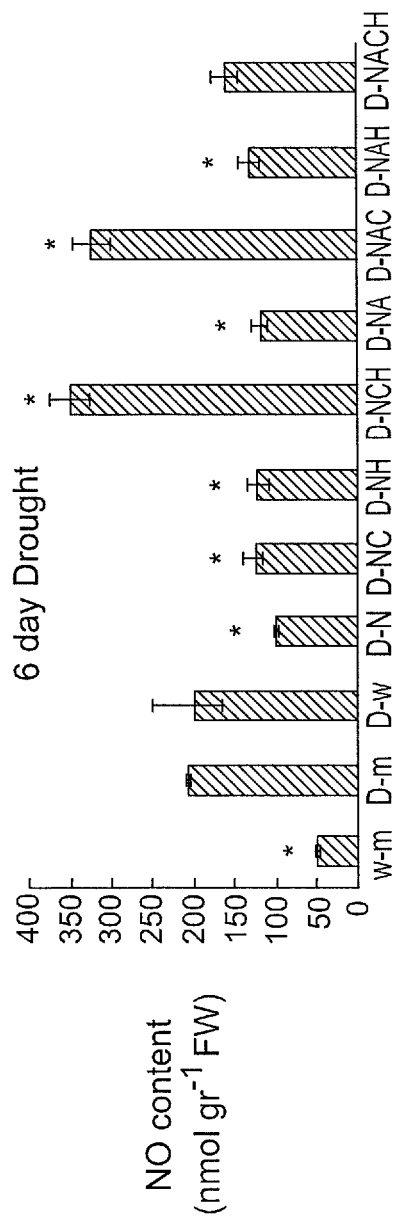

Abiotic stress conditions are associated with increased levels of reactive oxygen (ROS) and reactive nitrogen (RNS) species content, which are toxic for the cells. During such conditions, the production of ROS and RNS exceeds the capacity of the antioxidative defense systems to remove them, causing nitro-oxidative stress. Quantification of $H_2O_2$ (major ROS) and nitric oxide (NO; major RNS) content revealed a massive induction in drought-stressed plants, which was significantly reversed in NOSH and NOSH-aspirin pretreated plants compared with drought-stressed samples (FIG. 14A, B). Interestingly, $H_2O_2$ content was ameliorated even further in NOSH and NOSH-A pretreated plants following rewatering at 7 d compared with respective pretreated, drought-stressed samples at 6 d (FIG. 14A), indicating an improved capacity to recover which also correlates with increased CAT enzymatic activity following rewatering in these samples compared with drought-stressed alone samples (FIG. 16B).

Proline Content

In addition, proline content was evaluated as proline is a major osmoprotective molecule involved in the defense response of plants to abiotic stress conditions (Filippou et al., 2013). Results showed drought stress imposition leads to massive proline induction as expected (Filippou et al, 2014), while pretreatment of plants with NOSH and NOSH-A prior to drought stress imposition resulted in significantly lower proline content compared with drought-stressed alone samples (FIG. 15).

Antioxidant Enzymes

Figures 2, 14B:
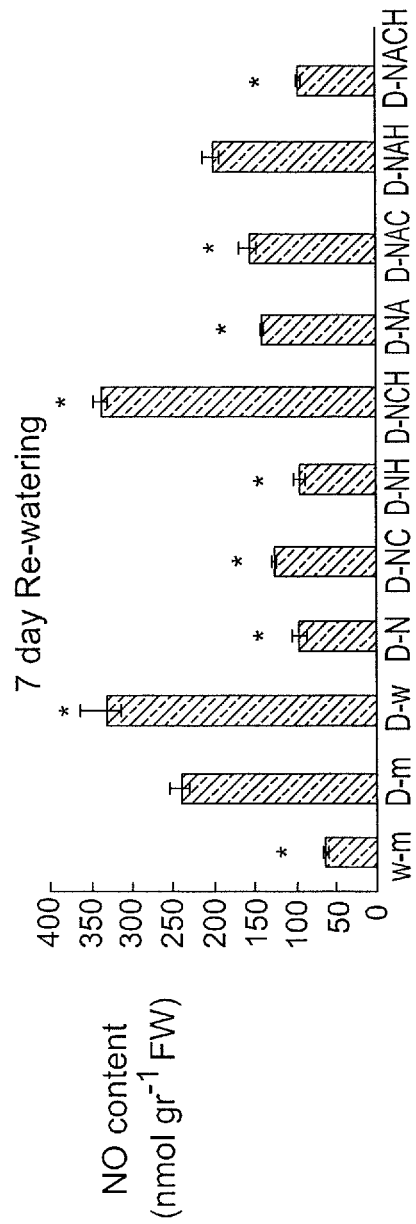

The enzymatic activity of two key antioxidants (SOD and CAT) were evaluated. SOD dismutates superoxide radicals to hydrogen peroxide, while CAT directly scavenges hydrogen peroxide. Both enzymes appear to be regulated in response to stress and priming agent pretreatment in a differential manner (FIG. 16). More specifically, activity of both SOD and CAT is significantly induced in 6 d drought-stressed plants compared with control, watered plants, likely in an attempt to tackle the oxidative burst resulting from stress imposition, whereas NOSH and NOSH-A pretreated and subsequently stressed plants show similar SOD and CAT activity levels to control, watered plants. Interestingly, rewatering results in a reversal of trends, where SOD and CAT activity is significantly induced in primed and stressed plants compared with stressed-alone plants, suggesting an improved capacity to recover which also correlates with further lowered $H_2O_2$ levels (FIG. 14). In any case, it should be noted that the cellular enzymatic antioxidant battery linked with ROS scavenging is very complex involving several other components (e.g. APX), isoforms in several compartments (e.g. peroxisomes, chloroplasts, mitochondria), as well as non-enzymatic antioxidants (e.g. ascorbic acid, tocopherols and glutathione).

Gene Expression Analysis

Figure 17A:
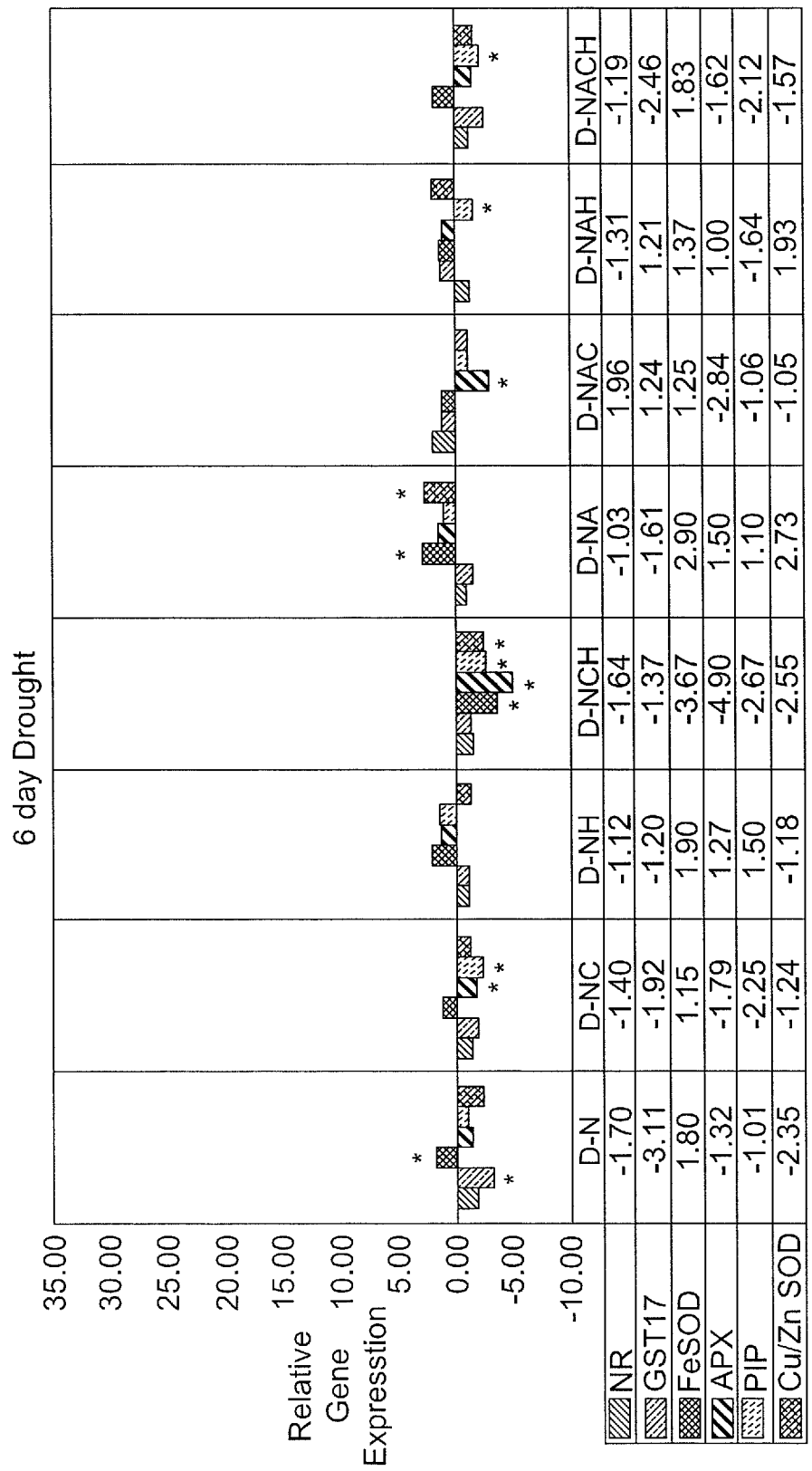
FIG. 17 Real-time RT-PCR relative gene expression in leaves of drought-stressed *M. sativa* plants in the presence or absence of NOSH/NOSH-aspirin pretreatment at 6 d (drought stress) and 7 d (recovery) compared with control plants. NR=nitrate reductase, GST17=glutathione S-transferase 17, Cu/ZnSOD=Cu/Zn superoxide dismutase, FeSOD=Fe superoxide dismutase, APX=cytosolic ascorbate peroxidase, PIP=aquaporin.
Figure 17B:
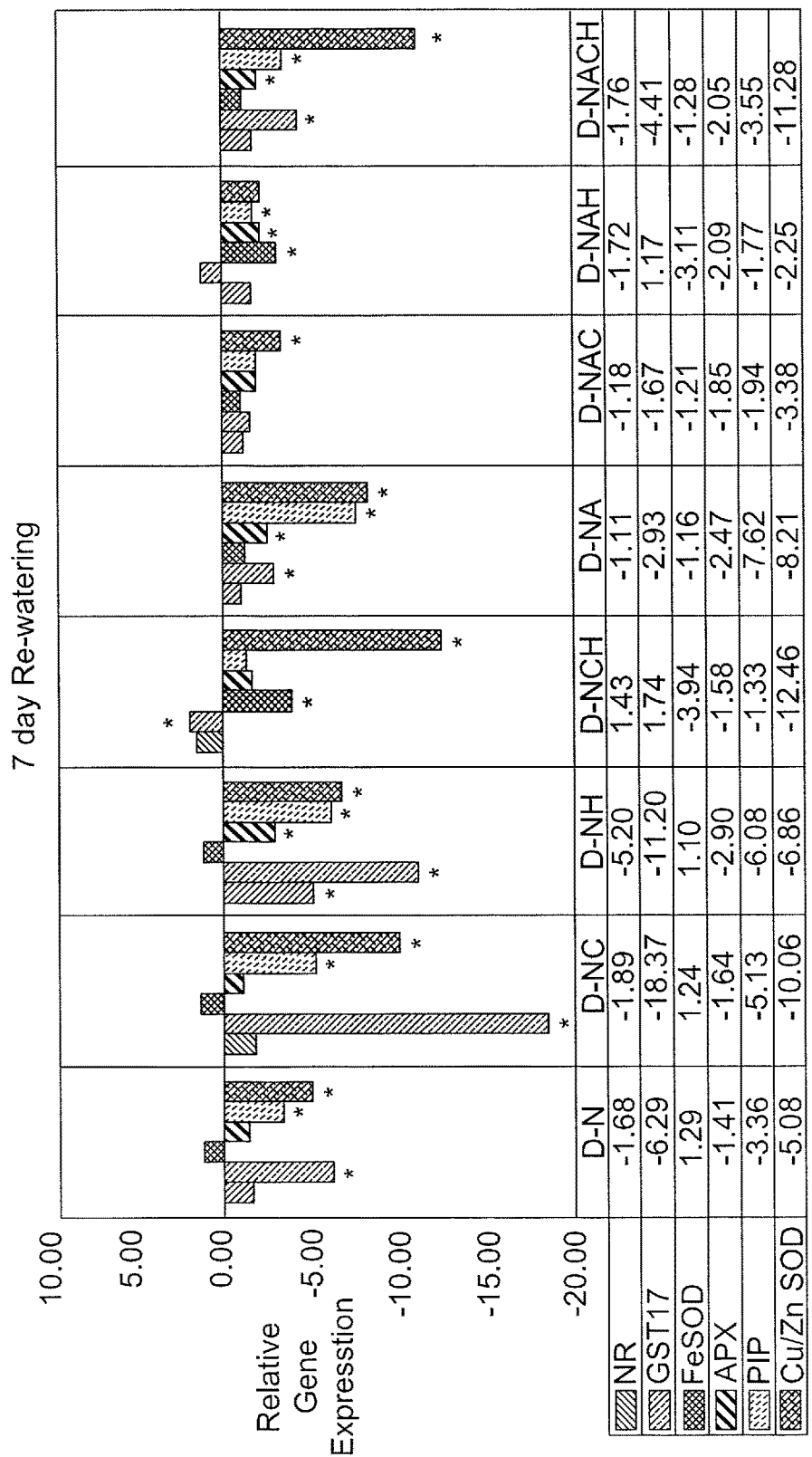
Figure 18:
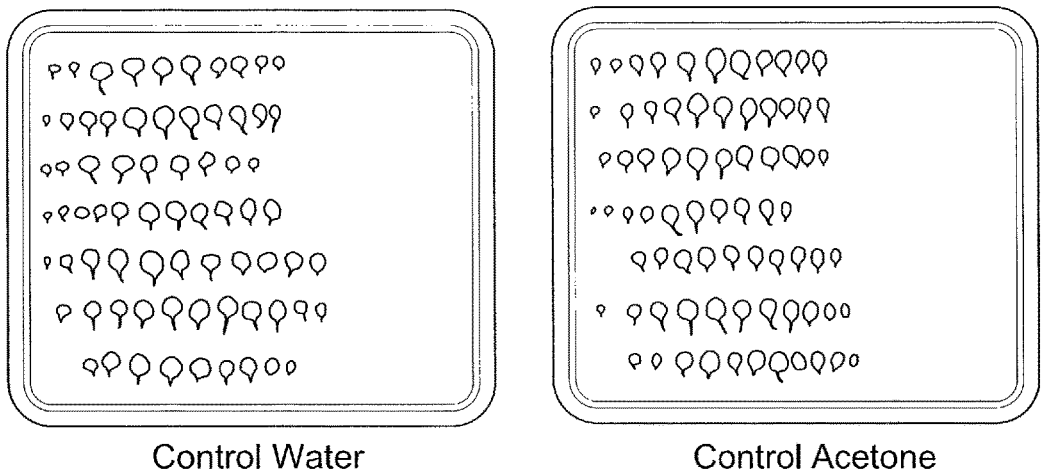
FIG. 18 Leaf series of individual plants treated with water or 20% (v/v) acetone.
Figure 19:
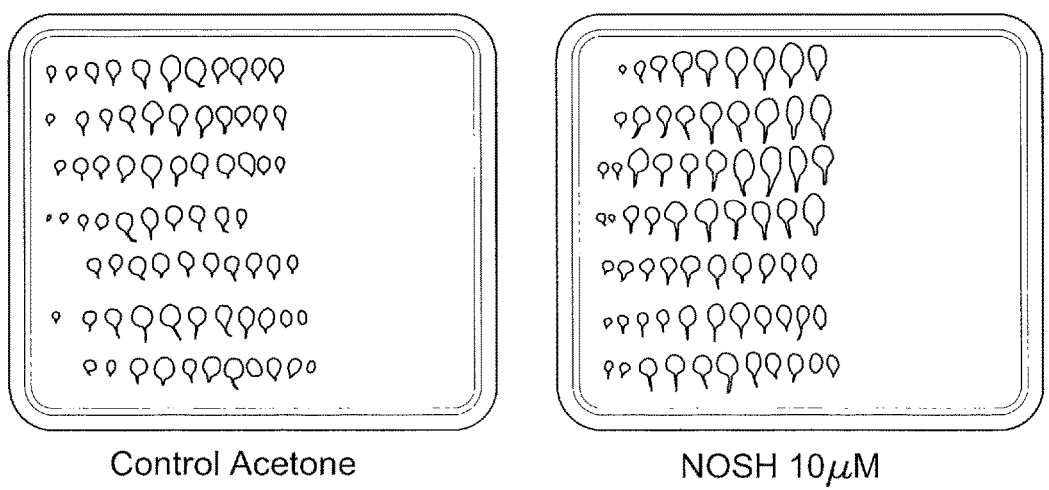
FIG. 19 Leaf series of individual plants treated with 10 µM NOSH.
Figure 20:
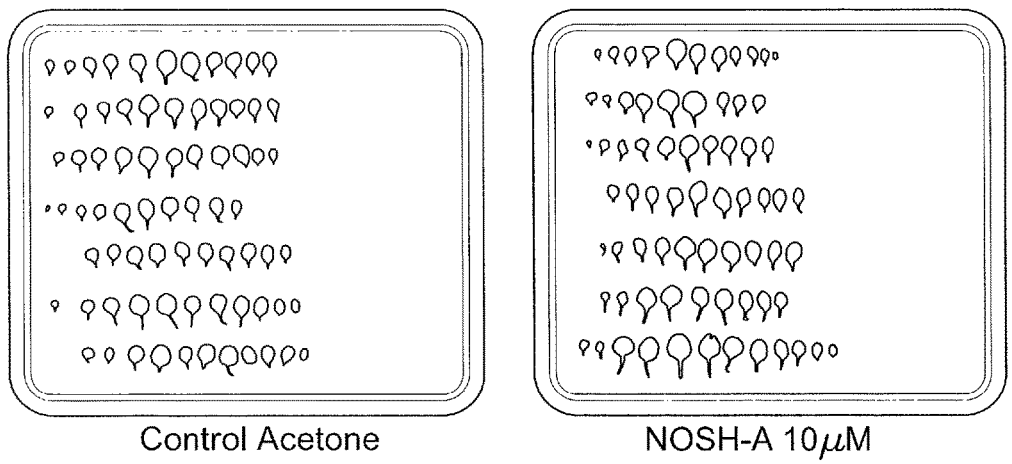
FIG. 20 Leaf series of individual plants treated with 10 µM NOSH-A.
Figure 21:
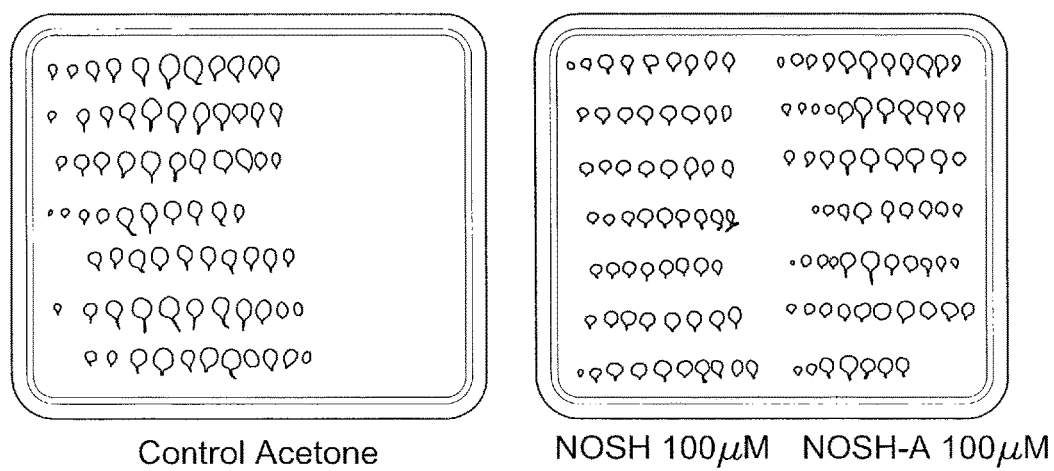
FIG. 21 Leaf series of individual plants treated with 100 µM NOSH or NOSH-A.

Finally, qRT-PCR gene expression analysis was carried out (FIG. 17) for key defense-related genes, including major enzymatic antioxidants (GST17, Cu/ZnSOD, FeSOD, cAPX) linked with ROS scavenging, as well as genes involved in NO biosynthesis (NR). In addition, an aquaporin (PIP) was also examined which is linked with response to water deficit and transport. Interestingly, NOSH and NOSH-A pretreated and subsequently stressed plants compared with stressed alone plants demonstrated significant transcriptional regulation (induction) for SOD isoforms (FIG. 17) which are linked with dismutation of superoxide radicals to $H_2O_2$, in agreement with a recent report by Fotopoulos et al. (2014), who demonstrated that treatment with 100 μM of NO donor sodium nitroprusside results in significant induction of FeSOD in mature *Medicago truncatula* plants. In addition, it should be noted that rewatering resulted in general suppression of most genes examined in NOSH/NOSH-A pretreated and subsequently stressed plants compared with drought-stressed alone plants, suggesting that the plants are in a better position to recover without the further transcriptional activation of defense-related genes which is energy consuming for the plant.

Conclusions

The current findings show NOSH and NOSH-aspirin's capacity to provide significant protection in Medicago sativa plants against drought stress conditions, which result in major cellular damage and nitro-oxidative stress in control plants.

Example 3

An in vitro experiment was carried out in order to evaluate the potential of NOSH and NOSH-A for growth promotion in terms of leaf area increase in *Arabidopsis thaliana* plants.

Experimental setup

*Arabidopsis thaliana* Col-0 plants were used for the purposes of this study. Seeds were placed on MS agar plates containing 10 μM or 100 μM NOSH or NOSH-A (diluted in 20% (v/v) acetone) which were then incubated in the dark at 4° C. for 4 days for stratification purposes. Appropriate control plates were also prepared. The plates were then placed in a growth chamber and leaves were sampled at 23 DAS (days after sowing). Complete leaf series were examined from seven individual plants per treatment (n=7). A complete leaf series consists of all leaves from each individual plant, starting from the cotyledons and including all true leaves, harvested and examined in order of presence on the plant (from older to younger true leaf). These leaves are excised and placed on agar plates where photographs are taken and leaf areas are calculated using ImageJ software (http://imagej.nih.gov/ij/).

Results and Discussion

FIGS. 18-21 are the plates of all examined leaf series. Acetone controls are used in order to examine the effect of the organic solvent itself on the growth of plants.

An interesting observation is that the specific NOSH-treated plants displayed increased greening, suggesting higher levels of photosynthetic pigments.

Figure 22:
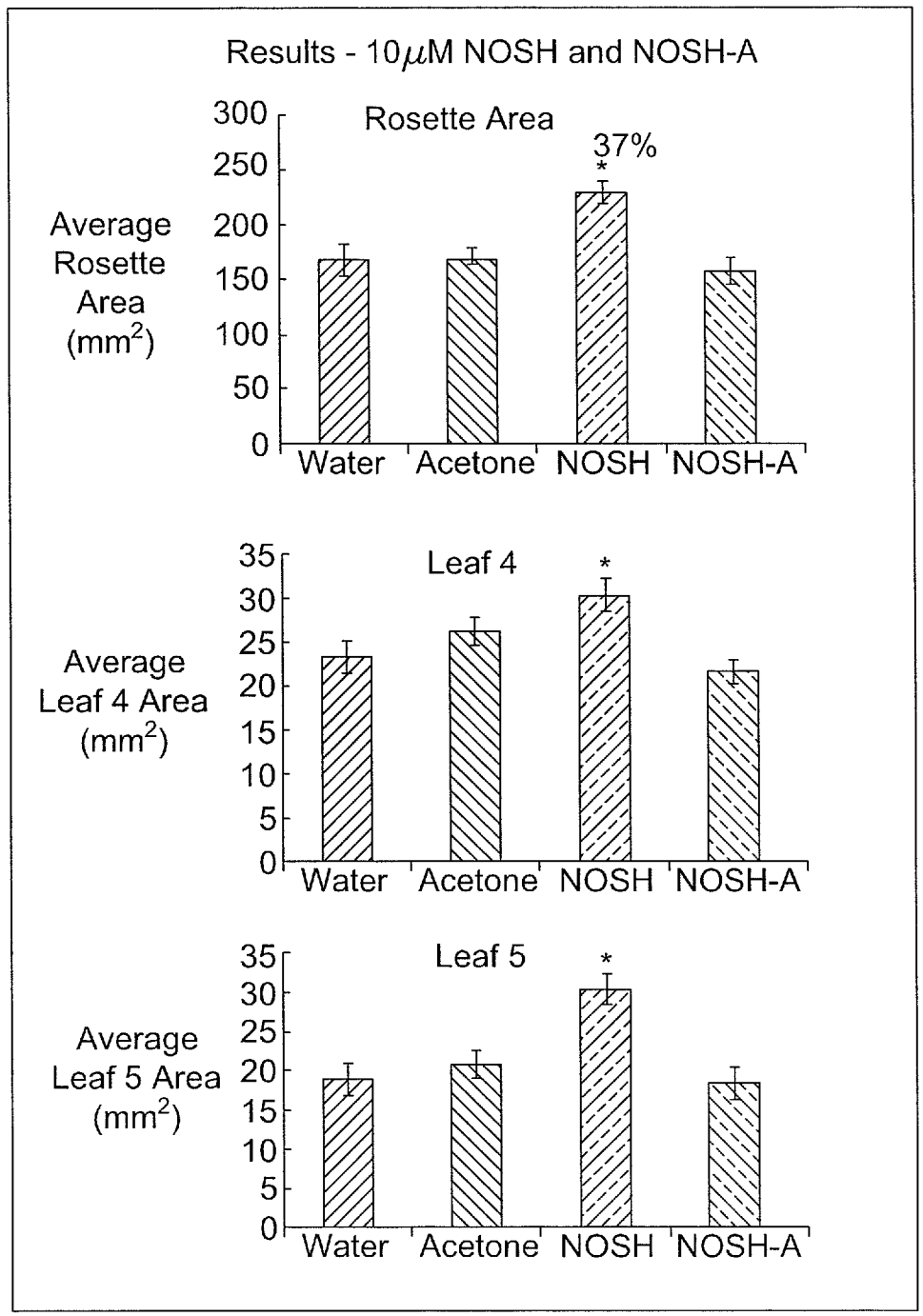
FIG. 22 Leaf area analysis of control plants and plants treated with 10 µM NOSH or NOSH-A. Rosette area indicates the total leaf area per plant (leaves form a rosette at the base of the plant—any leaves that might appear on the flowering stem are not included in the rosette, although leaves are normally not developed along the stem by 23 DAS when sampling takes place).

ImageJ leaf area analysis was carried out for control plants and plants treated with 10 μM NOSH or NOSH-A as macroscopic analysis revealed visible growth induction in this case, contrarily to plants treated with 100 μM NOSH or NOSH-A. See FIG. 22.

Results show that there is significantly higher true leaf 4 and 5 area in plants treated with 10 μM NOSH compared with control samples, while no significant increase was observed in NOSH-A treated plants. Interestingly, the overall rosette area (total leaf area per plant) is significantly increased by 37% in NOSH-treated plants compared with control plants.

Conclusions

The current findings suggest that 10 μM NOSH application results in significant induction in growth in terms of leaf area in in vitro grown plants.

The invention claimed is:

1. A method of reducing cellular damage to a plant comprising treating the plant with composition comprising a compound containing an NO-releasing moeity and an $H_2S$-releasing moiety covalently bonded to an aspirin derived core of formula I:

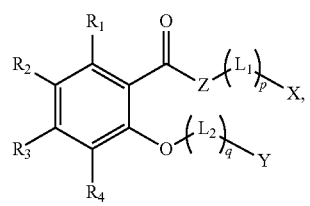

wherein:
each of p and q, independently, is 0 or 1;
each of $L_1$ and $L_2$, independently, is a linker, the linker being —C(O)—, —$(CH_2)_m$—, —$(CH_2)_m$—O—, —$(CH_2)_m$—C(O)—, —$(CH_2)_m$—C(O)O—, —$(CH_2)_m$—OC(O)O—, —C(O)—$(CH_2)_m$—O—, —C(O)—$(CH_2)_m$—C(O)—, —OC(O)—$(CH_2)_m$—O—, —OC(O)—$(CH_2)_m$—C(O)—, or —OC(O)—$(CH_2)_m$—C(O)O—, in which m is 1, 2, 3, 4, 5, 6, or 7;
X is a $H_2S$-releasing moiety or a NO-releasing moiety;
Y is a NO-releasing moiety or a $H_2S$-releasing moiety, provided that X and Y are not simultaneously $H_2S$-releasing moieties or NO-releasing moieties;
Z is O or NH; and
each of $R_1$, $R_2$, $R_3$, and $R_4$, independently, is H, halo, $C_1$-$C_{10}$ alkyl, or $N(R)_2$, in which R is H or $C_1$-$C_{10}$ alkyl.

2. A method according to claim 1, wherein the $H_2S$-releasing moiety is

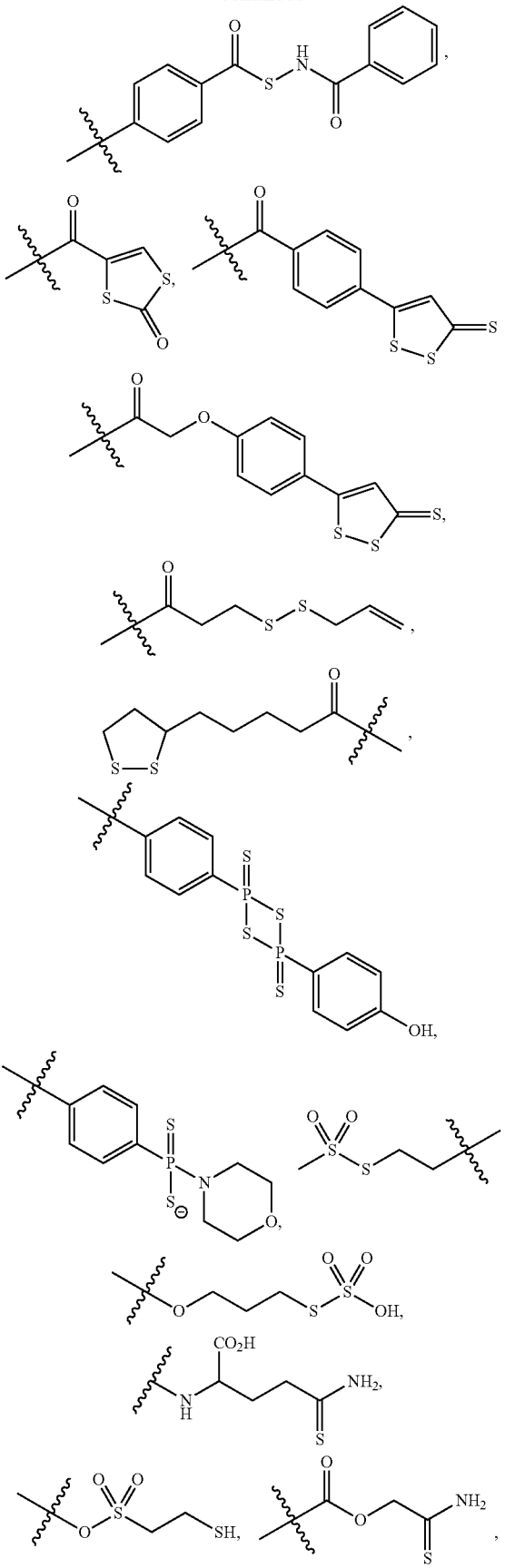

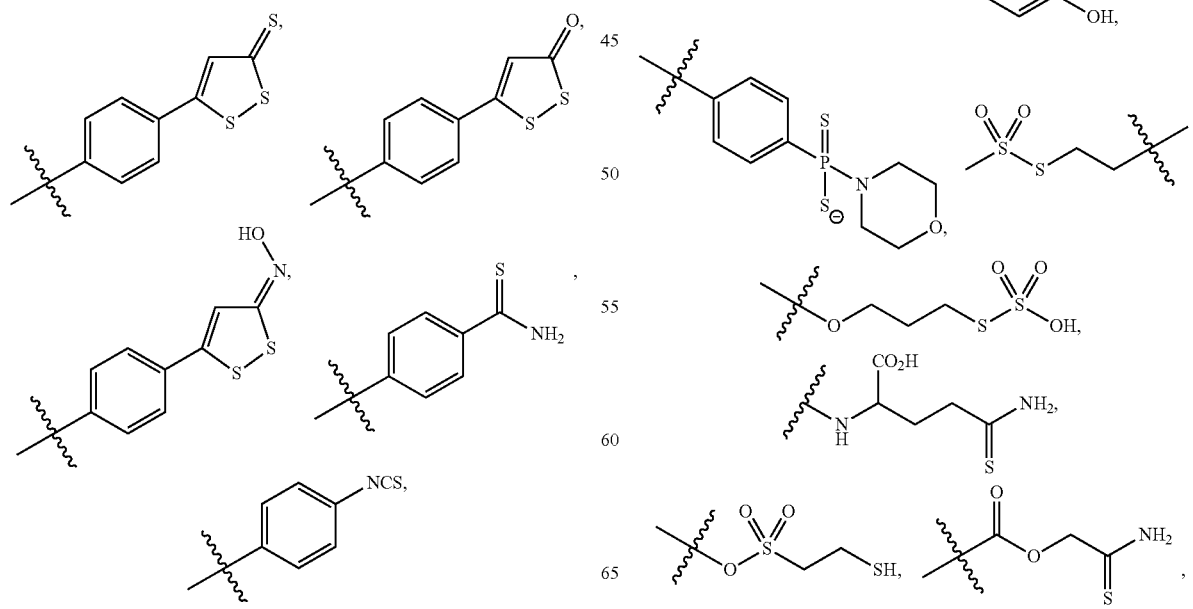

and the NO-releasing moiety is —NO, —C(O)—(CH$_2$)$_n$—ONO$_2$, —O—(CH$_2$)$_n$—ONO$_2$, —(CH$_2$)$_n$—ONO$_2$, —C(O)—CH$_2$—C(CH$_3$)$_2$—SNO, —NH—CH$_2$—C(CH$_3$)$_2$—SNO, —CH$_2$—C(CH$_3$)$_2$—SNO, in which n is 1, 2, 3, 4, 5, 6, or 7; $R_a$ is H, $C_1$-$C_{10}$ alkyl, aryl, S(O)$_2$-aryl, CN, or CON($R_b$)$_2$; and each $R_b$, independently, is H or $C_1$-$C_{10}$ alkyl.

3. A method according to claim 2, wherein X is

4. A method according to claim 3, wherein Y is —C(O)—(CH$_2$)$_n$—ONO$_2$.

5. A method according to claim 1, wherein the compound is

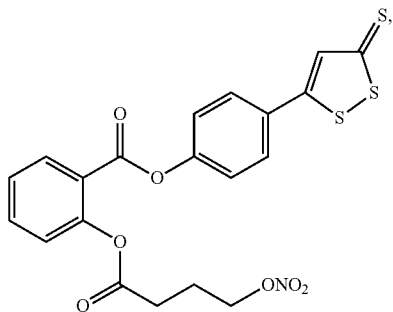

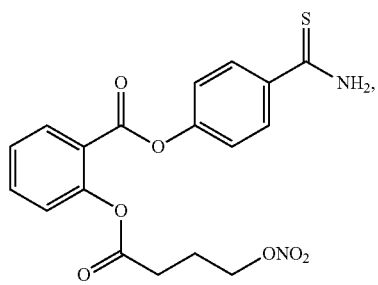

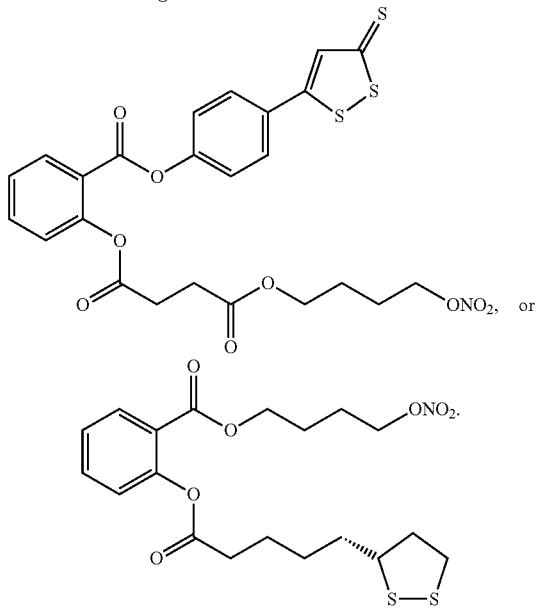

or

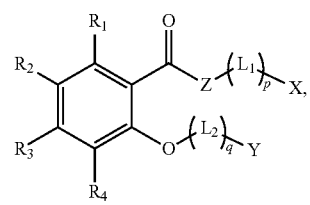

6. A method of priming a plant against abiotic stress factors comprising treating the plant with a composition comprising a compound containing an NO-releasing moiety and an H$_2$S-releasing moiety covalently bonded to an aspirin derived core of formula I:

(I)

wherein:

each of p and q, independently, is 0 or 1;

each of L$_1$ and L$_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7;

X is a H$_2$S-releasing moiety or a NO-releasing moiety;

Y is a NO-releasing moiety or a H$_2$S-releasing moiety, provided that X and Y are not simultaneously H$_2$S-releasing moieties or NO-releasing moieties;

Z is O or NH; and each of R$_1$, R$_2$, R$_3$, and R$_4$, independently, is H, halo, C$_1$-C$_{10}$ alkyl, or N(R)$_2$, in which R is H or C$_1$-C$_{10}$ alkyl.

7. The method according to claim 6, wherein the abiotic stress factor is drought, salinity, heat, or combinations thereof.

8. A method according to claim 6, wherein the H$_2$S-releasing moiety is

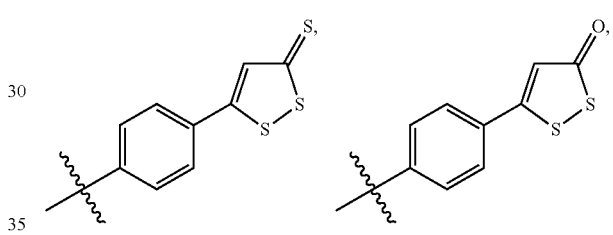

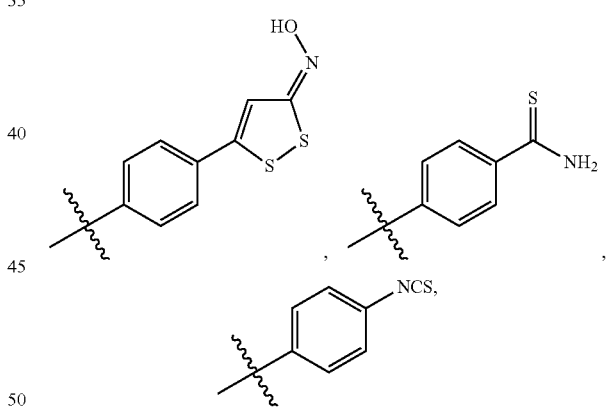

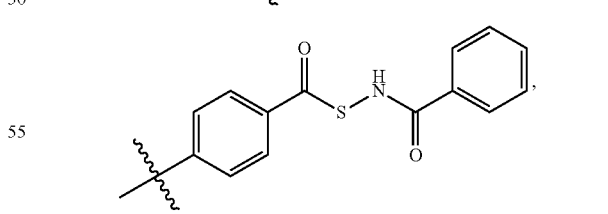

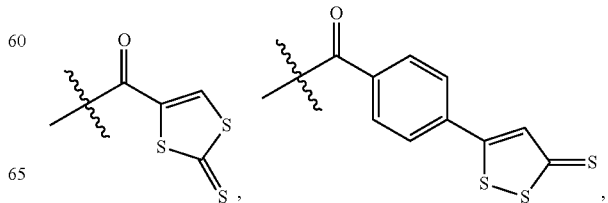

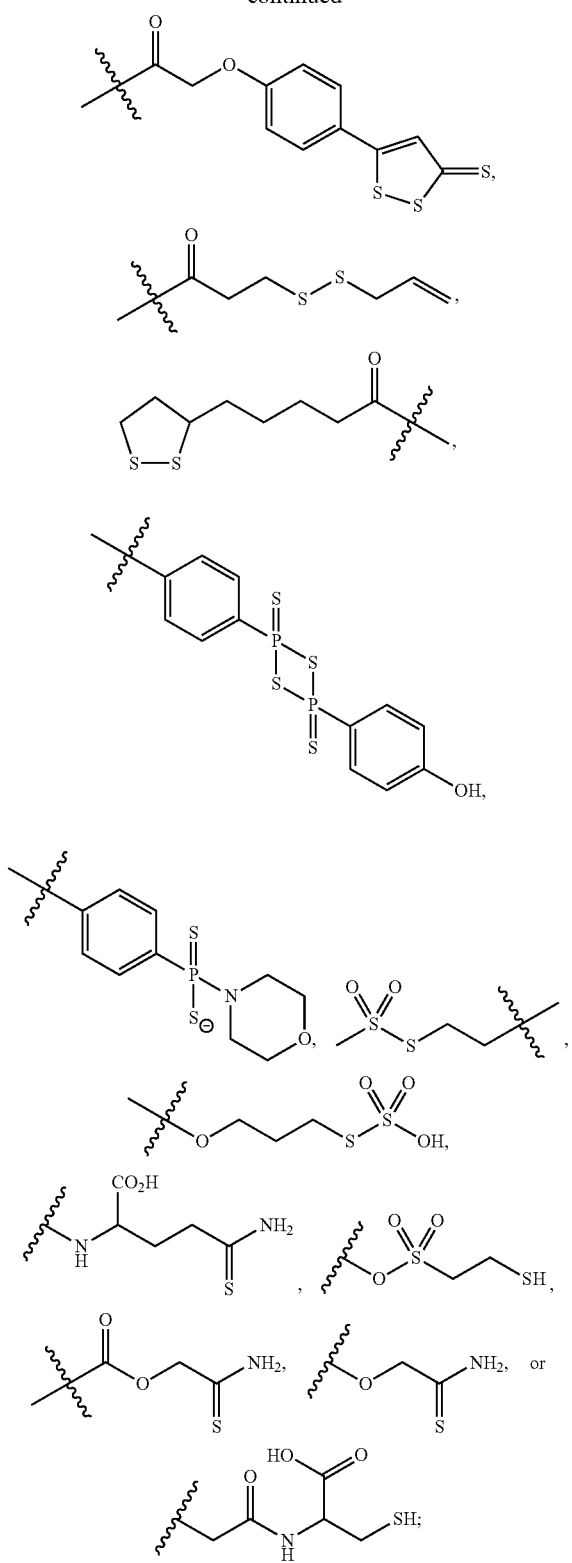
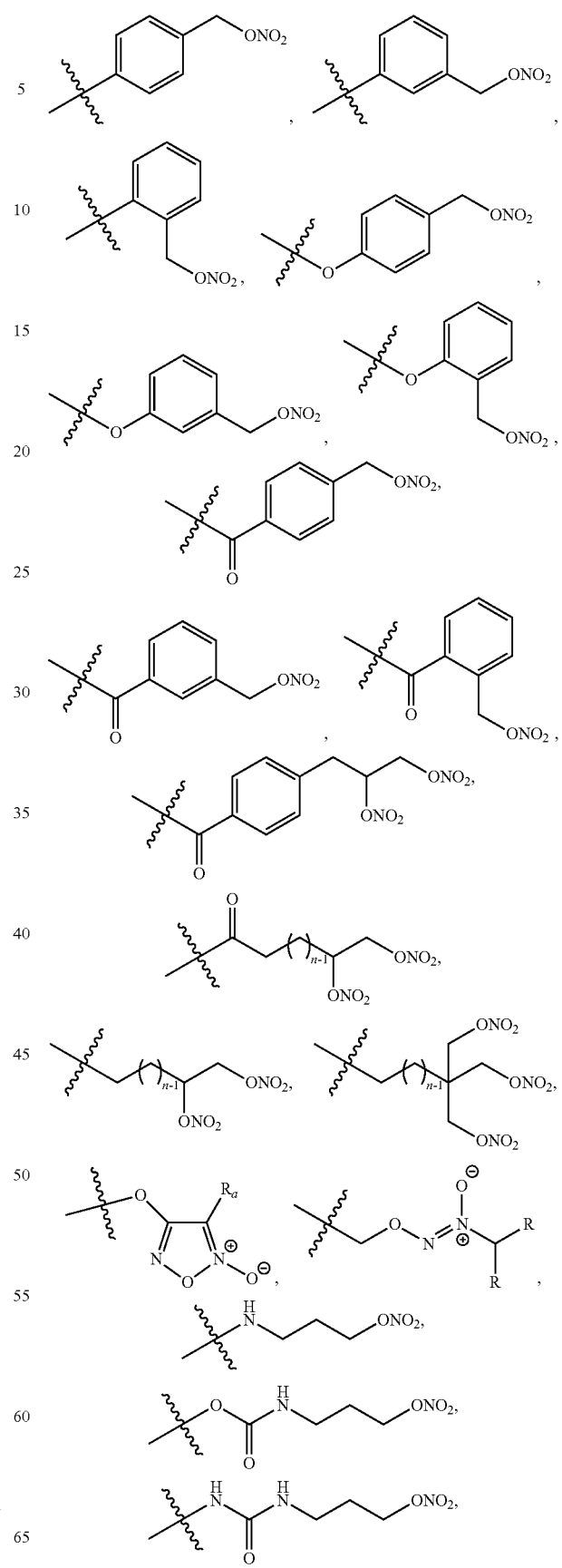
and
the NO-releasing moiety is —NO, —C(O)—(CH$_2$)$_n$—ONO$_2$, —O—(CH$_2$)$_n$—ONO$_2$, —(CH$_2$)$_n$—ONO$_2$, —C(O)—CH$_2$—C(CH$_3$)$_2$—SNO, —NH—CH$_2$—C(CH$_3$)$_2$—SNO, —CH$_2$—C(CH$_3$)$_2$—SNO, -continued

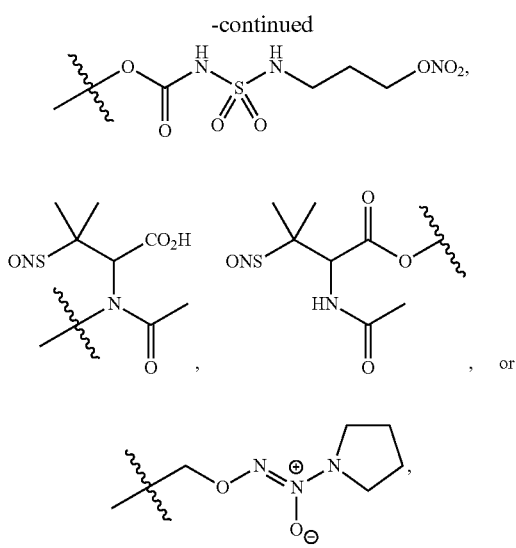

in which n is 1, 2, 3, 4, 5, 6, or 7; $R_a$ is H, $C_1$-$C_{10}$ alkyl, aryl, $S(O)_2$-aryl, CN, or $CON(R_b)_2$; and each $R_b$, independently, is H or $C_1$-$C_{10}$ alkyl.

9. A method according to claim 8, wherein X is

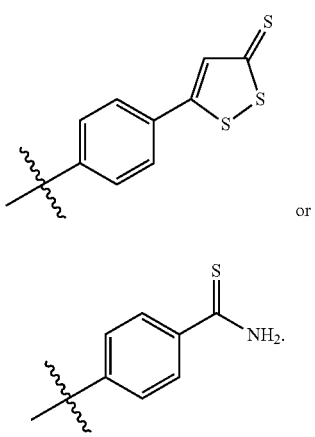

10. A method according to claim 9, wherein Y is —C(O)—(CH$_2$)$_n$—ONO$_2$.

11. A method according to claim 6, wherein the compound is

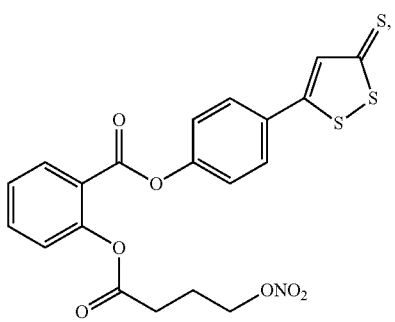

-continued

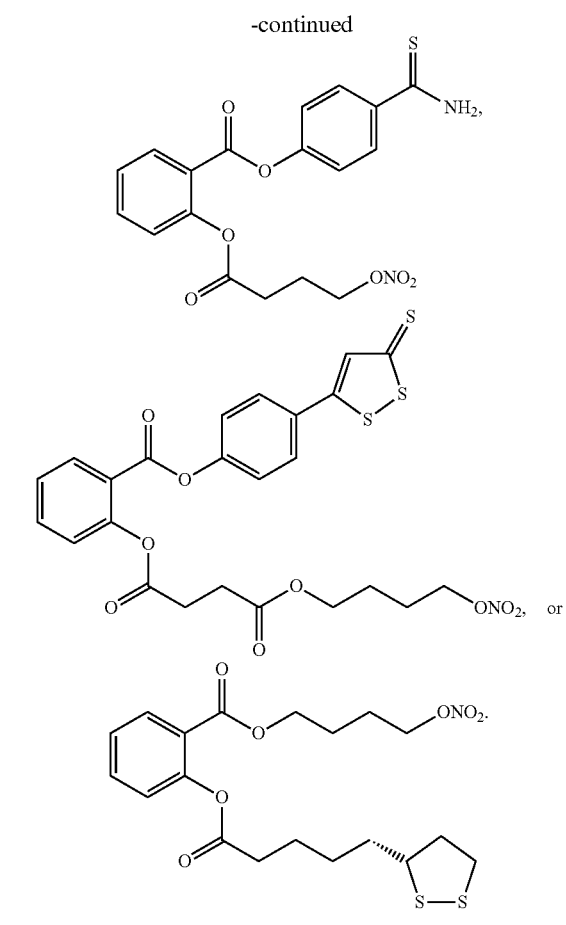

12. A method of reducing cellular damage to a plant comprising treating the plant with a composition comprising a compound of the following structure:

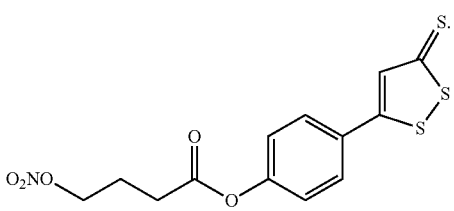

13. A method of priming a plant against abiotic stress factors comprising treating the plant with a composition comprising a compound of the following structure:

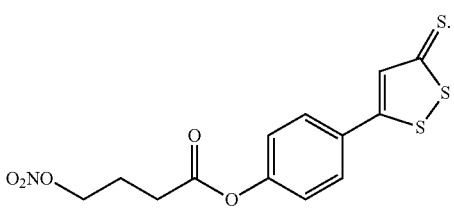

14. A method of promoting growth of a plant comprising treating the plant with a composition comprising a compound containing an NO-releasing moiety and an H$_2$S- releasing moiety covalently bonded to an aspirin derived core or a compound of the following structure:

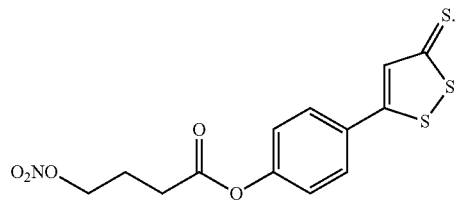

15. A method according to claim 14, wherein the compound containing an NO-releasing moiety and an H$_2$S-releasing moiety covalently bonded to an aspirin derived core is of formula I:

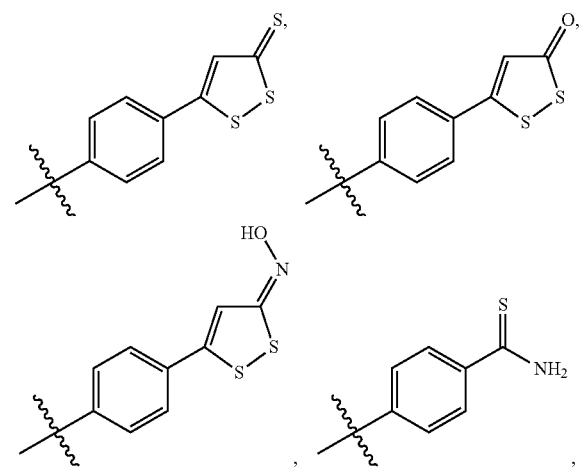

wherein:
each of p and q, independently, is 0 or 1;
each of L$_1$ and L$_2$, independently, is a linker, the linker being —C(O)—, —(CH$_2$)$_m$—, —(CH$_2$)$_m$—O—, —(CH$_2$)$_m$—C(O)—, —(CH$_2$)$_m$—C(O)O—, —(CH$_2$)$_m$—OC(O)O—, —C(O)—(CH$_2$)$_m$—O—, —C(O)—(CH$_2$)$_m$—C(O)—, —OC(O)—(CH$_2$)$_m$—O—, —OC(O)—(CH$_2$)$_m$—C(O)—, or —OC(O)—(CH$_2$)$_m$—C(O)O—, in which m is 1, 2, 3, 4, 5, 6, or 7;
X is a H$_2$S-releasing moiety or a NO-releasing moiety;
Y is a NO-releasing moiety or a H$_2$S-releasing moiety, provided that X and Y are not simultaneously H$_2$S-releasing moieties or NO-releasing moieties;
Z is O or NH; and
each of R$_1$, R$_2$, R$_3$, and R$_4$, independently, is H, halo, C$_1$-C$_{10}$ alkyl, or N(R)$_2$, in which R is H or C$_1$-C$_{10}$ alkyl.

16. A method according to claim 15, wherein the H$_2$S-releasing moiety is

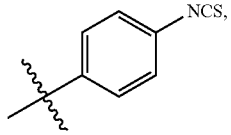
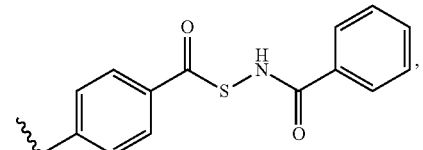
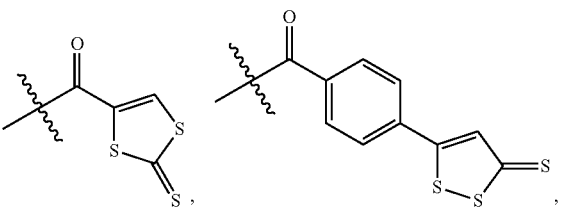
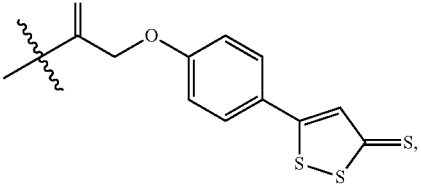
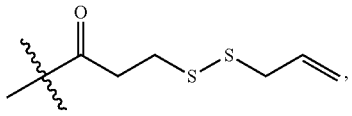
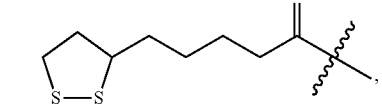
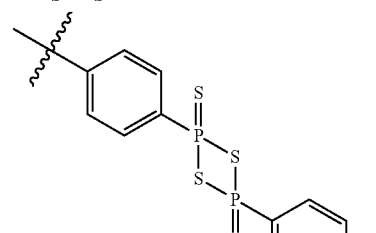
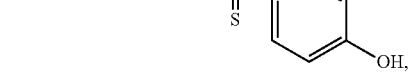
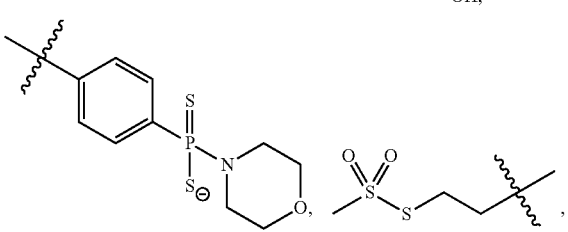
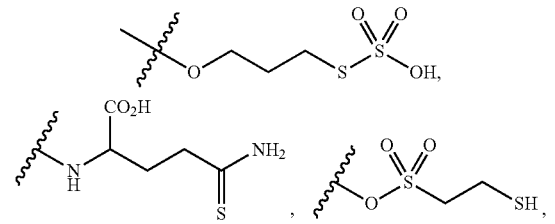
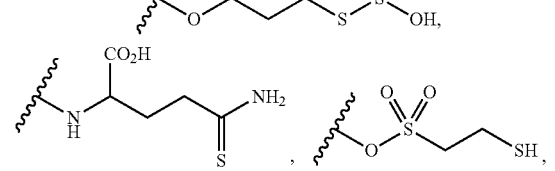

-continued

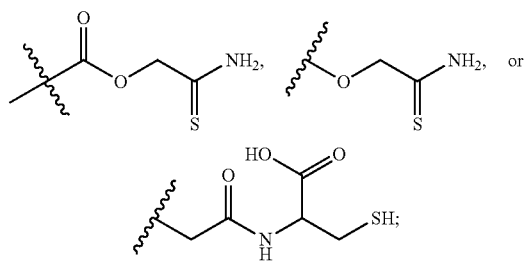

and the NO-releasing moiety is —NO, —C(O)—(CH$_2$)$_n$—ONO$_2$, —O—(CH$_2$)$_n$—ONO$_2$, —(CH$_2$)$_n$—ONO$_2$, —C(O)—CH$_2$—C(CH$_3$)$_2$—SNO, —NH—CH$_2$—C(CH$_3$)$_2$—SNO, —CH$_2$—C(CH$_3$)$_2$—SNO,

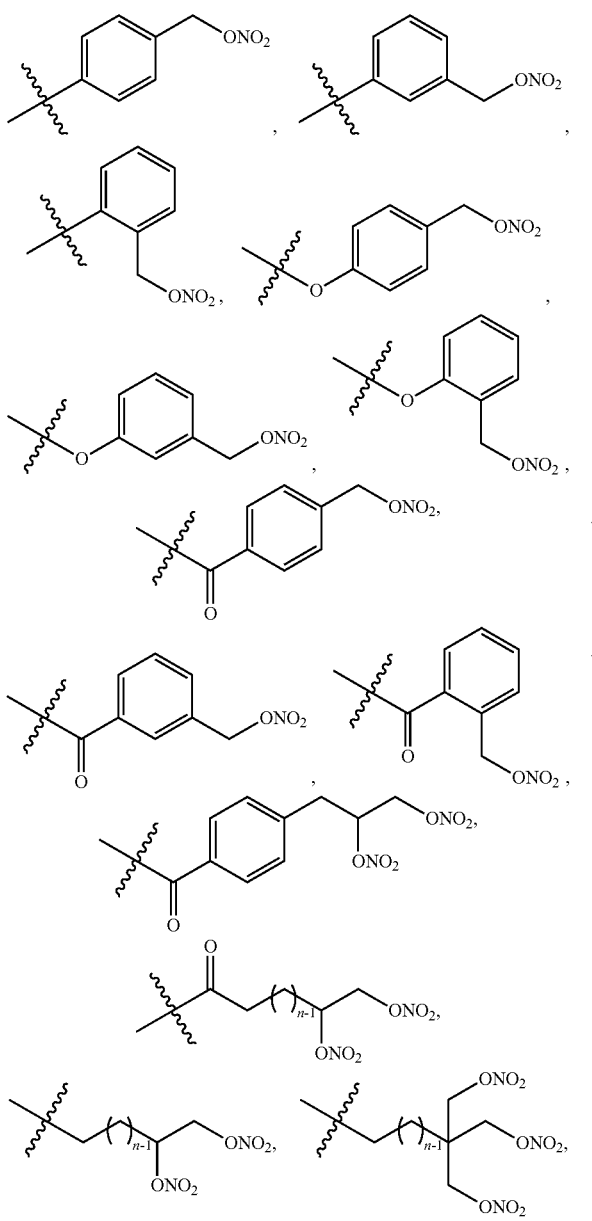

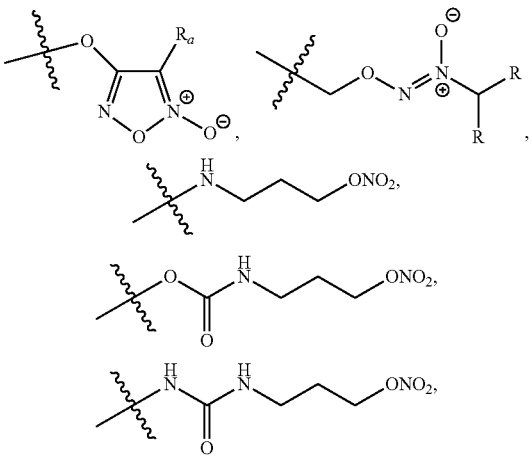

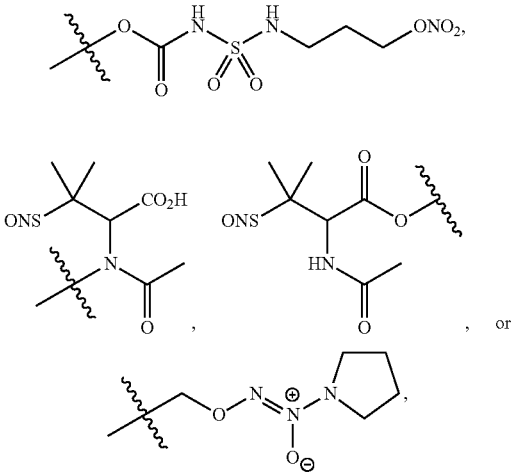

in which n is 1, 2, 3, 4, 5, 6, or 7; R$_a$ is H, C$_1$-C$_{10}$ alkyl, aryl, S(O)$_2$-aryl, CN, or CON(R$_b$)$_2$; and each R$_b$, independently, is H or C$_1$-C$_{10}$ alkyl.

17. A method according to claim 15, wherein X is

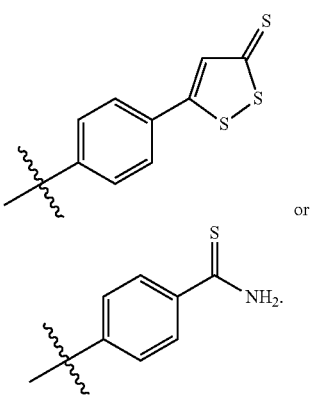

18. A method according to claim 15, wherein Y is —C(O)—(CH$_2$)$_n$—ONO$_2$.

19. A method according to claim 15, wherein the compound is

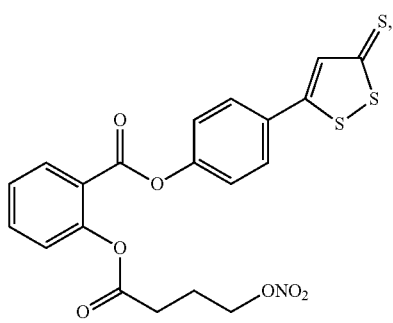
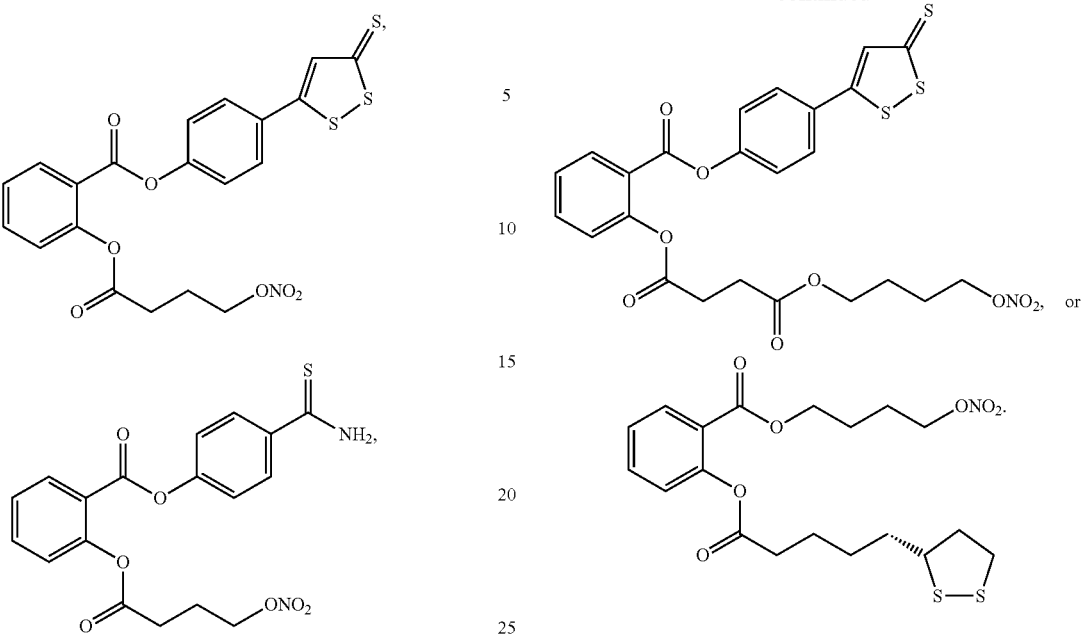

UNITED STATES PATENT AND TRADEMARK OFFICE
CERTIFICATE OF CORRECTION

| | |
|---|---|
| PATENT NO. | : 10,071,981 B2 |
| APPLICATION NO. | : 15/115959 |
| DATED | : September 11, 2018 |
| INVENTOR(S) | : Kashfi et al. |

Page 1 of 1

It is certified that error appears in the above-identified patent and that said Letters Patent is hereby corrected as shown below:

In the Claims
Column 40, Line 15 of Claim 1:
NOW READS:

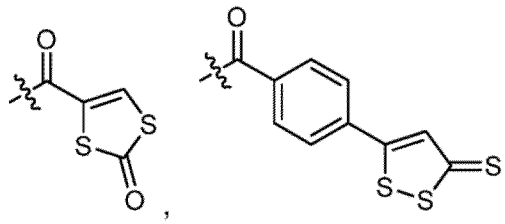

SHOULD READ:

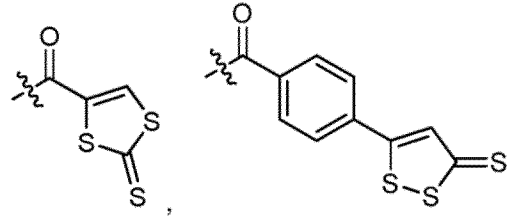

Signed and Sealed this
Sixth Day of August, 2019

Andrei Iancu
*Director of the United States Patent and Trademark Office*